US007888030B2

(12) United States Patent
Butt et al.

(10) Patent No.: US 7,888,030 B2
(45) Date of Patent: Feb. 15, 2011

(54) BIOMARKERS

(75) Inventors: Asif Naeem Butt, Reading (GB); Ramasamyiyer Swaminathan, Radlett (GB)

(73) Assignees: King's College London, London (GB); Guy's & St. Thomas's NHS Foundation Trust, London (GB)

( * ) Notice: Subject to any disclaimer, the term of this patent is extended or adjusted under 35 U.S.C. 154(b) by 104 days.

(21) Appl. No.: 12/195,979

(22) Filed: Aug. 21, 2008

(65) Prior Publication Data

US 2010/0047779 A1    Feb. 25, 2010

(51) Int. Cl.
*C12Q 1/68* (2006.01)
(52) U.S. Cl. .......................................... 435/6
(58) Field of Classification Search ........................ None
See application file for complete search history.

(56) References Cited

U.S. PATENT DOCUMENTS 5,075,212 A    12/1991 Rotbart

OTHER PUBLICATIONS

Abdal et al. (2006) The Eye in Sleep Apnea Syndrome, Sleep Med. 7:107-115.
Agalou et al. (2008) Hypertension and Circulating mRNA for 11β-Hydroxysteroid Dehydrogenase Type II, Ann. N.Y. Acad. Sci. 1137:290-295.
Bakir et al. (2008) Circulating 11β-Hydroxysteroid Dehydrogenase Type 1 mRNA and Cardiovascular Risk Factors, Ann. N.Y. Acad. Sci. 1137:283-289.
Beaucage et al. (1981) Deoxynucleoside Phosphoramidites—A New Class of Key Intermediates for Deoxypolynucleotide Synthesis, Tetrahedron Letts. 22:1859-1862.
Bruley et al. (2006) A Novel Promoter for the 11β-Hydroxysteroid Dehydrogenase Type 1 Gene is Active in Lung and is C/EBPα independent, Endocrinology 147(6):2879-2885.
Bujalska et al. (1997) Does Central Obesity Reflect "Cushing's Disease of the Omentum"?, Lancet 349:1210-1213.
Butt et al. (2006) Circulating Nucleic Acids and Diabetic Complications, Ann. N.Y. Acad. Sci., 1075:258-270.
Caputo et al. (1994) Assessment and Management of Foot Disease in Patients with Diabetes, N. Engl. J. Med. 331(13):854-860.
Carr (2003) The Emergence of Metabolic Syndrome With Menopause, J. Clin. Endocrinol. Metab. 88(6):2404-2411.
Chan et al. (2003) Cell-Free Nucleic Acids in Plasma, Serum and Urine: A New Tool in Molecular Diagnosis, Ann. Clin. Biochem. 40:122-130.
Chen et al. (2000) Telomerase RNA as a Detection Marker in the Serum of Breast Cancer Patients, Clin. Cancer Res. 6:3823-3826.
Cope et al. (1958) The Production Rate of Cortisol in Man, British Medical Journal 14:1020-1024.
De Gooyer et al. (2006) Rod Photoreceptor Loss in Rho -/- Mice Reduces Retinal Hypoxia and Hypoxiaregulated Gene Expression, Invest. Opthalmol. Vis. Sci. 47(12):5553-5560.
Dieudonn'e et al. (2006) Sex Steroids and Leptin Regulate 11β-Hydroxysteroid Dehydrogenase I and P450 Aromatase Expression in Human Preadipocytes: Sex Specificities, J. Steroid Biochem. Mol. Biol. 99:189-196.
Draper et al. (2005) 11β Hydroxysteroid Dehydrogenase and Pre-Receptor Regulation of Corticosteroid Hormone Action, J. Endocrinol. 186:251-271.
Egger et al. (1995) Reverse Transcription Multiplex PCR for Differentiation Between Polio-and Enteroviruses From Clinical and Environmental Samples, J. Clin. Microbiol. 33(6):1442-1447.
Fandrey (2004) Oxygen-Dependent and Tissue-Specific Regulation of Erythropoietin Gene Expression, Am. J. Physiol. Regul. Integr. Comp. Physiol. 286:R977-R988.
GenBank Accession No. NM-000196, Mar. 14, 2010.
GenBank Accession No. NM-000329, Mar. 14, 2010.
GenBank Accession No. NM-000330, Mar. 5, 2010.
GenBank Accession No. NM-000364, Mar. 14, 2010.
GenBank Accession No. NM-000539, Mar. 14, 2010.
GenBank Accession No. NM-001975, Mar. 14, 2010.
Gomez-Sanchez et al. (2003) Regulation of 11β-Hydroxysteroid Dehydrogenase Enzymes in the Rat Kidney by Estradiol, Am. J. Physiol. Endocrinol. Metab. 285:E272-E279.
Gooch et al. (2004) The Diabetic Neuropathies, Neurologist 10(6):311-322.
Greijer et al. (2005) Up-Regulation of Gene Expression by Hypoxia is Mediated Predominantly by Hypoxia-Inducible Factor 1 (HIF-1), J. Pathol. 206:291.
Hasse et al. (1984) Methods in Virology, vol. VII, Chapter 7, Detection of Viral Nucleic Acids by *in Situ* Hybridization, pp. 189-226.
Halicka et al. (2000) Segregation of RNA and Separate Packaging of DNA and RNA in Apoptotic Bodies During Apoptosis, Experimental Cell Research, 260:248-256.
Hamaoui et al. (2004) Concentration of Circulating Rhodopsin mRNA in Diabetic Retinopathy, Clin. Chem. 50:2152-2155.
Hamaoui et al. (2004) Real-Time Quantitative PCR Measurement of Circulatory Rhodopsin mRNA in Healthy Subjexts and Patients With Diabetic Retinopathy, Ann. N.Y. Scad. Sci. 1022:152-156.
Hannibal (2006) Regulation of Melanopsin Expression, Chronobiol. Int. 23:159-166.
Hargrave (2001) Rhodopsin Structure, Function, and Topography: the Friedenwald Lecture, Invest. Ophthalmol. Vis. Sci. 42(1):3-9.
Holzer et al. (1998) Costs and Duration of Care for Lower Extremity Ulcers in Patients with Diabetes, Clin. Ther. 20(1):169-181.
Ishiguro et al. (1983) Nervous System-Specific Enolase in Serum as a Marker for Neuroblastoma, Pediatrics, 72:696-700.

(Continued)

*Primary Examiner*—Young J Kim
(74) *Attorney, Agent, or Firm*—Morgan, Lewis & Bockius LLP

(57) ABSTRACT

The present invention provides circulating biomarkers for conditions associated with metabolic syndrome, including diabetes mellitus, hypertension and congestive heart failure. The biomarkers include plasma DNA, neuron-specific enolase, 11β-hydroxysteroid dehydrogenase, rhodopsin, retinoschisin, RPE65 and cardiac troponin T. Methods and kits for detecting these biomarkers in the prediction, monitoring and diagnosing of disease are provided, particularly for determining mRNA levels thereof in a subject's blood.

8 Claims, 18 Drawing Sheets

OTHER PUBLICATIONS

Kaiser et al. (1989) Clinical Biochemistry of Neuron Specific Enolase, Clin. Chim. Acta 183:13-31.
Kato et al. (1982) Distribution of Nervous System Specific Forms of Enolase in Peripheral Tissues, Brain Research 237:441-448.
Kaur et al. (2006) Early Response of Neurons and Glial Cells to Hypoxia in the Retina, Invest. Ophthalmol. Vis. Sci. 47(3): 1126-1141.
Knott et al. (2003) Diabetic Eye Disease, in Textbook of Diabetes, J. Pickup and G. Williams (eds.), Blackwell Publishing, Oxford, 3rd Edition, vol. 48, 1-48.
Li et al. (2004) Real-Time Quantitative PCR Measurement of Thyroglobulin mRNA in Peripheral Blood of Thyroid Cancer Patients and Healthy Subjects, Ann. N.Y. Acad. Sci., 1022:147-151.
Li et al. (2005) Chronic Intermittent Hypoxia Upregulates Genes of Lipid Biosynthesis in Obese Mice, J. Appl. Physiol. 99:1643-1648.
Lifton (1996) Molecular Genetics of Blood Pressure Variation, Science 272:676-680.
Lo et al. (2004) The Biological and Diagnostic Applications of Plasma RNA, Ann. N.Y. Acad. Sci. 1022:135-139.
Lo et al. (2004) The Biological and Diagnostic Applications of Plasma RNA, Ann. N.Y. Acad. Sci. 1022:135-139.
Marangos et al. (1987) Neuron Specific Enolase, a Clinically Useful Marker for Neurons, Ann. N.Y. Acad. Sci. and Neuroendocrine Cells, Annu. Rev. Neurosci. 10:269-295.
Marangos et al. (1979) Measurement of Neuronspecific (NSE) and Non-Neuronal (NNE) Isoenzymes of Enolase in Rat, Monkey and Human Nervous Tissue, J. of Neurochem. 33:319-329.
Marcus et al. (2001) Sleep Disorders: A Risk Factor for Normal-Tension Glaucoma? J. Glaucoma 10:177-183.
Maser et al. (2006) 11β-Hydroxysteroid Dehydrogenase Type 1: Purification From the Liver and Characterization as Carbonyl Reductase of Xenobiotics, Molecular and Cellular Endocrinology 248:34-37.
Maslim et al. (1997) Tissue Oxygen During a Critical Developmental Period Controls the Death and Survival of Photoreceptors, Invest. Ophthalmol. Vis. Sci. 38(9):1667-1677.
Mata et al. (2004) Rpe65 is a Retinyl Ester Binding Protein that Presents Insoluble Substrate to the Isomerase in Retinal Pigment Epithelial Cells, J. Biol. Chem. 279(1):635-643.
McColm et al. (2004) VEGF Isoforms and Their Expression After a Single Episode of Hypoxia or Repeated Fluctuations Between Hyperoxia and Hypoxia: Relevance to Clinical ROP, Molecular Vision, 10:512-520.
Miura et al. (2003) Sensitive Detection of Human Telomerase Reverse transcriptase mRNA in the Serum of Patients With Hepatocellular Carcinoma, Oncology 64:430-434.
Moiseyev et al. (2005) RPE65 is the Isomerohydrolase in the Retinoid Visual Cycle, PNAS 102(35):12413-12418.
Molday (2007) Focus on Molecules, Retinoschisin (RS1), Exp. Eye Res. 84:227-228.
Molday et al. (2001) Expression of X-Linked Retinoschisis Protein RS1 in Photoreceptor and Bipolar Cells, Invest. Ophthalmol. Vis. Sci. 42:816-825.
Nammi et al. (2006) Increased 11β-Hydroxysteroid Dehydrogenase Type-1 and Hexose-6-Phosphate Dehydrogenase in Liver and Adipose Tissue of Rat Offspring Exposed to Alcohol in Utero, Am. J. Physiol. Regul. Integr. Comp. Physiol. 292:R1101-R1109.
Nash et al. (1994) The Response of Cultured Human Retinal Pigment Epithelium to Hypoxia: A Comparison to Other Cell Types, Invest. Opthalmol. Vis. Sci., 35:2850-2856.
Needham-Van Devanter et al. (1984) Characterization of an Adduct Between CC-1065 and a Defined Oligodeoxynucleotide Duplex, Nucleic Acids Research, 12(15):6159-6168.
Netzer et al. (2001) Overnight Pulse Oximetry for Sleep-Disordered Breathing in Adults: A Review, Chest, 120:625-633.
Nolte (1998) Branched DNA Signal Amplication for Direct Quantitation of Nucleic Acid Sequences in Clinical Specimens, Adv. Clin. Chem. 33:201-235.
Odermatt et al. (2006) Why is 11β-Hydroxysteroid Dehydrogenase Type 1 Facing the Endoplasmic Reticulum Lumen? Physiological Relevance of the Membrane Topology of 11β-HSD1, Molecular Cellular Endocrinology, 248:15-23.
Ollendorft et al. (1998) Potential Economic Benefits of Lower-Extremity Amputation Prevention Strategies in Diabetes, Diabetes Care, 21(8):1240-1245.
Pearson et al. (1983) High Performance Anion-Exchange Chromatography of Oligonucleotides, J. Chrom. 255:137-149.
Peirson et al. (2006) Melanopsin: Another Way of Signaling Light, Neuron, 49:331-339.
Pepe et al. (1999) Cloning of the 11β-Hydroxysteroid Dehydrogenase (11β-HSD)-2 Gene in the Baboon: Effects of Estradiol on Promoter Activity of 11β-HSD-1 and -2 in Placental JEG-3 Cells, Biochim. Biophys. Acta 1444:101-110.
Peters et al. (2007) Identification of Appropriate Patients for Cardiometabolic Risk Management, Reviews in Cardiovascular Medicine 8(Suppl. 4):S9-S16.
Pirart (1997) Diabetes Mellitus and Its Degenerative Complications: A Prospective Study of 4400 Patients Observed Between 1947-1973 (third and last part), Diabetes Metab. 3:245-256.
Poch et al. (2001) Evaluation of Renin-Angiotensin-Aldosterone System Gene Polymorphisms, Hypertension 38:1204.
Rainen et al. (2002) Stabilization of nRNA Expression in Whole Blood Samples, Clin. Chem. 48(11):1883-1890.
Rainer et al. (2003) Prognostic Use of Circulating Plasma Nucleic Acid Concentrations in Patients With Acute Stroke, Clin. Chem. 49(4):562-569.
Ramsey et al. (1999) Incidence, Outcomes, and Costs of Foot Ulcers in Patients With Diabetes, Diabetes Care, 22(3):382-387.
Rask et al. (2001) Tissue-Specific Dysregulation of Cortisol Metabolism in Human Obesity, J. Endocrinol. Metab. 86:1418-1421.
Rask et al. (2002) Tissue Specific Changes in Peripheral Cortisol Metabolism in Obese Women: Increased Adipose 11β-Hydroxysteroid Dehydrogenase Type 1 Activity, J. Clin. Endocrinol. Metab. 87:3330-3336.
Redmond et al. (1998) RPE65 is Necessary for Production of 11-Cis-Vitamin A in the Retinal Visual Cycle, Nature Genetics, 20:344-351.
Reid et al. (2003) Retinoschisin, a Photoreceptor-Secreted Protein and Its Interaction With Bipolar and Muller Cells, J. Neurosci. 23(14):6030-6040.
Reid et al. (1999) The Mouse X-Linked Juvenile Retinoschisis cDNA Expression in Photoreceptors, gene 227:257-266.
Riddle et al. (1993) Acute Reduction of Renal 11β-Hydroxysteroid Dehydrogenase Activity by Several Anti-Natriuretic Stimuli, Metabolism 42:1370-1374.
Rith-Najarian et al. (1998) Reducing Lower Extremity Amputations Due to Diabetes: Application of the Staged Diabetes Management Approach in Primary Care Setting, J. Fam. Pract. 47:127-132.
Romero et al. (1993) Diagnostic Molecular Biology: Principles and Applications, Persing (ed.) Mayo Foundation, Rochester, N.Y., pp. 401-406.
Rosi et al. (1988) RNA-lipid Complexes Released From the Plasma Membrane of Human Colon Carcinoma Cells, Cancer Lett. 39:153-160.
Sandhu et al. (2008) Measurement of Circulating Neuron-Specific Enolase mRNA in Diabetes Mellitus, Ann. N.Y. Acad. Sci 1137:258-263.
Schmechel et al. (1978) Brain Enolases as Specific Marker of Neuronal and Glial Cells, Science 199(4326):313-315.
Semenza (2004) Hydroxylation of HIF-1: Oxygen Sensing at The Molecular Level, Physiology 19:176-182.
Shalchi et al. (2008) Retina-Specific mRNA in the Assessment of Diabetic Retinopathy, Ann. N.Y. Acad. Sci. 1137:253-257.
Sinclair et al. (2005) Diabetic Retinopathy: Treating Systemic Conditions Aggressively Can Save Sight, Cleveland Clin. J. Med. 72(5):447-454.
Singer et al. (1986) Optimization of In Situ Hybridization Using Isotopic and Non-Isotopic Detection Methods, Biotechniques, 4(3):230-250.
Stewart (1996) 11β-Hydroxysteroid Dehydrogenase: Implications for Clinical Medicine, Clin. Endocrinol. 44:493-499.
Stewart et al. (1999) Cortisol Metabolism in Human Obesity: Impaired Cortisone to Cortisol Conversion in Subjects With Central Adiposity, J. Clin. Endocrinol. Metab. 84(3):1022-2017.

Stockmann et al. (2006) Hypoxia-Induced Erythropoeitin Production: A Paradigm for Oxygen Regulated Gene Expression, Clin. Exp. Pharmacol. Physiol. 33:968-979.

Strauss (2005) The Retinal Pigment Epithelium in Visual Function, Physiol. Rev. 85:845-881.

Stroun et al. (1989) Neoplastic Characteristics of the DNA found in the Plasma of Cancer Patients, Oncology, 46(5):318-322.

Tamkovich et al. (2005) Concentration of Extracellular DNA and Deoxyribonuclease Activity in Human Blood, Clin Chem 51(7):1317-1319.

The Sixth Report of the Joint National Committee on Prevention, Detection, Evaluation, and Treatment of High Blood Pressure (JNC VII), Arch. Intern. Med. 157:2413-2446, (1997).

Tomlinson et al. (2005) Mechanisms of Disease: Selective Inhibitor of 11β-Hydroxysteroid Dehydrogenase Type 1 as a Novel Treatment for the Metabolic Syndrome, Nature Clin. Practice Endocrinology Metabolism 1(2):92-99.

Tomlinson et al. (2004) 11β-Hydroxysteroid Dehydrogenase Type 1: A Tissue Specific Regulator of Glucocorticoid Response, Endocrine Reviews, 25(5):831-866.

Tsang et al. (2006) Moderate to Severe Obstructive Sleep Apnoea in Patients is Associated with a Higher Incidence of Visual Field Defect, Eye, 20:38-42.

Valentino et al. (1995) Alcohol Inhibits 11β-Hydroxysteroid Dehydrogenase Activity in Rat Kidney and Liver, Horm. Res. 43:176-180.

Valter et al. (1998) Photoreceptor Dystrophy in the RCS Rat: Roles of Oxygen, Debris, and bFGF, Invest. Ophthalmol. Vis. Sci. 39:2427-2442.

Vijan et al. (2000) Cost-Utility Analysis of Screening Intervals for Diabetic Retinopathy in Patients With Type 2 Diabetes Mellitus, JAMA, 283:889-896.

Walker et al. (2006) Tissue Production by Cortisol by 11β-Hydroxysteroid Dehydrogenase Type 1 and Metabolic Disease, Ann. N.Y. Acad. Sci. 1083:165-184.

Wangsa-Wirawan et al. (2003) Retinal Oxygen: Fundamental and Clinical Aspects, Arch. Opthalmol. 121:547-557.

White et al. (1997) 11β-Hydroxysteroid Dehydrogenase and the Syndrome of Apparent Mineralocorticoid Exess, Endocrine Rev. 18(1):135-156.

Wijeratne et al. (2004) Cell-Free Plasma DNA as a Prognostic Marker in Intensive Treatment Unit Patients, Ann. N.Y. Acad. Sci, 102:232-238.

Wolf (2005) Function of the Protein RPE65 in the Visual Cycle, Nutr. Rev. 63:97-100.

World Health Organisation, International Society of Hypertension Group 2003. 2003 World Health Organisation (WHO)/International Society of Hypertension (ISH) Statement on Management on Hypertension, Journal of Hypertension, 21(11):1983-1992.

Zhang et al. (2001) Effects of Alcohol on Blood Pressure and Production of Vascular Aldersterone and Corticosterone, Horn. Res. 55:245-248.

US 7,888,030 B2

BIOMARKERS

SEQUENCE LISTING SUBMISSION VIA EFS-WEB

A computer readable text file, entitled "670245010SeqList.txt," created on or about Nov. 9, 2010 with a file size of about 5 kb contains the sequence listing for this application and is hereby incorporated by reference in its entirety.

FIELD OF THE INVENTION

The present invention relates to biomarkers which are indicative of a condition associated with metabolic syndrome.

BACKGROUND

The metabolic syndrome relates to a combination of disorders which is found at high prevalence in many populations, and which consequently presents a major global health challenge. Metabolic syndrome is particularly characterised by hyperglycemia hypertension, hypertriglyceridaemia and obesity, and has been linked to cardiovascular disease and diabetes.

Fasting hyperglycemia, i.e. elevated blood glucose, is an important characteristic of metabolic syndrome. Subjects showing the metabolic syndrome may vary in the degree of hyperglycemia, and the severity of this condition may progress over time. Thus the hyperglycemia found in metabolic syndrome patients may result from a condition classified as impaired fasting glucose, impaired glucose tolerance or insulin resistance.

Many patients with metabolic syndrome are diagnosed with full type 2 diabetes mellitus (adult-onset diabetes). Type 2 diabetes is characterised by a fasting plasma glucose level of 7.0 mmol/l or higher. Type 2 diabetes is commonly caused by insulin resistance coupled with a deficiency in pancreatic insulin production. Uncontrolled diabetes may result in serious complications such as neuropathy, retinopathy and nephropathy. Diabetic retinopathy is a major cause of blindness in the developed world. Insulin resistance is thus closely associated with both the metabolic syndrome and diabetes mellitus, as well as its complications.

Insulin resistance is also linked to abnormalities in blood lipids, such as a high level of free fatty acids and triglycerides, which are commonly found together in metabolic syndrome. These factors, together with high LDL cholesterol, low HDL cholesterol and high blood pressure are major risk factors for the development of atherosclerosis and consequently various cardiovascular disorders. Many of the above factors are typically present in subjects with metabolic syndrome, leading to an increased incidence of conditions such as coronary heart disease and stroke.

Coronary heart disease is a condition typically caused by narrowing and hardening of the coronary arteries (atherosclerosis). Atherosclerosis may result from accumulation of cholesterol within the walls of the coronary arteries. Coronary heart disease may lead to a heart attack (myocardial infarction), heart failure or chest pain (angina pectoris). Coronary atherosclerosis, and thus diseases such as congestive heart failure, are closely associated with the metabolic syndrome, as well as elevated LDL cholesterol and cigarette smoking. The individual risk factors present in the metabolic syndrome combine to greatly raise the risk for coronary heart disease.

The glucocorticoid hormones (cortisol, corticosterone) produced by the adrenal gland also have the potential to cause insulin resistance. Cushing's disease, which results from overproduction of glucocorticoids, commonly leads to insulin resistance and type 2 diabetes. Some patients treated with glucocorticoids, e.g. as anti-inflammatory agents, also show insulin resistance. 11β-hydroxysteroid dehydrogenases (11β-HSDs) catalyse the interconversion of active glucocorticoids such as cortisol and their inert forms such as cortisone. Whereas 11β-HSD type 1 is a predominant reductase in most intact cells which generates active cortisol from cortisone, 11β-HSD type 2 is a high affinity dehydrogenase that rapidly inactivates cortisol in kidney and colon.

A large number of therapies are available for controlling conditions associated with metabolic syndrome. For instance, ACE inhibitors and diuretics are commonly used to lower blood pressure and statins (HMG-CoA reductase inhibitors) have been shown to be effective in lowering LDL cholesterol. In many cases, the metabolic syndrome and its associated conditions can be alleviated by non-pharmacological interventions, such as a combination of improved diet, exercise and weight loss. However, a major problem is that metabolic syndrome, and in particular serious associated disorders and complications such as hypertension and diabetic retinopathy, often go undetected for long periods of time. Many patients only present for treatment at a stage when serious irreversible damage has been done. Even when subjects are clinically assessed for the first time, there is often a lack of quantitative methods for accurately assessing the progression and severity of particular disorders.

There is therefore a need for improved methods for assessing susceptibility of subjects to conditions associated with metabolic syndrome.

SUMMARY OF THE INVENTION

In one aspect, the present invention provides a method for assessing susceptibility to a condition associated with metabolic syndrome in a subject, comprising determining a level of one or more biomarkers in the subject's blood, wherein the biomarker comprises plasma DNA, neuron-specific enolase, 11β-hydroxysteroid dehydrogenase, rhodopsin, retinoschisin, RPE65 and cardiac troponin T, and wherein the level of the biomarker in the subject's blood is indicative of susceptibility to the condition.

In another aspect, the present invention provides a method for assessing susceptibility to a condition associated with metabolic syndrome in a subject, comprising determining a level of one or more mRNAs in the subject's blood, wherein the mRNA encodes a protein selected from a group consisting of neuron-specific enolase, 11β-hydroxysteroid dehydrogenase, rhodopsin, retinoschisin, RPE65 and cardiac troponin T, and wherein the level of the mRNA in the subject's blood is indicative of susceptibility to the condition.

In one embodiment, the level of the biomarker (e.g. mRNA) in the subject's blood is compared to a control level. For instance, the control level may represent a level of the biomarker or mRNA in the blood of a normal individual, i.e. a subject not suffering from the condition. Thus the method may comprise a further step of determining a control level of the biomarker or mRNA in a normal individual's blood, and comparing the control level to the level in the subject. In some embodiments, the level of the biomarker or mRNA (e.g. in the subject's blood and in a control sample) may be standardised against a standard marker such as β-actin.

A difference in the level of the biomarker (e.g. mRNA) in the subject's blood compared to the control may provide an indication of susceptibility to the condition. For instance, an increase or decrease in the level of the biomarker or mRNA in the subject may be indicative of an increase or a decrease in the subject's susceptibility to the condition.

By "assessing susceptibility" to a condition, it is meant that the method may comprise detecting the condition, diagnosing the condition, determining the severity of the condition, monitoring progress of the condition, determining a status of the condition or predicting the condition. Thus the present methods may be used, for example, to predict the likelihood of the condition developing in an individual at a future time as well as to detect the current presence of the condition. In specific embodiments, the methods may provide quantitative results which allow the progress of the condition to be continuously monitored, for instance to determine whether the condition is in an early or late stage of development or whether the individual is mildly, moderately or severely affected.

Conditions associated with metabolic syndrome include, but are not limited to, hyperglycemia, impaired fasting glucose, impaired glucose tolerance, insulin resistance, diabetes mellitus, diabetic neuropathy, diabetic retinopathy, diabetic nephropathy, hypoxic disorders, hypertriglyceridaemia, high LDL cholesterol, low HDL cholesterol, atherosclerosis, hypertension, coronary heart disease, myocardial infarction, congestive heart failure, angina pectoris and stroke.

In some embodiments, the condition associated with metabolic syndrome is selected from the group consisting of diabetes mellitus and cardiovascular disorders. In specific embodiments, the condition is selected from the group consisting of diabetic retinopathy, background diabetic retinopathy, preproliferative diabetic retinopathy, proliferative retinopathy, diabetes mellitus without retinopathy, diabetes mellitus with hypoxia, diabetic retinopathy with obstructive sleep apnea, hypertension and congestive heart failure.

The method may involve determining a level of the biomarker in the subject's blood by, for example, determining a level of the biomarker protein in the subject's blood. Alternatively, the method may involve determining a level of an mRNA encoding the biomarker protein in the subject's blood. In some embodiments, a level of the biomarker (i.e. mRNA or protein) may be determined in whole blood, i.e. in a sample of whole blood from the subject. In an alternative embodiment, the level may be determined in a blood fraction, i.e. in a component fraction separated from a blood sample. For instance, in one embodiment the level is determined in a cell-free sample, e.g. in plasma.

In one embodiment, the biomarker or protein is neuron-specific enolase (NSE). When the protein is NSE, the condition may be diabetes mellitus or a complication thereof, particularly type 2 diabetes mellitus. Diabetes complications include retinopathy, neuropathy and nephropathy. Changes in levels of blood NSE mRNA are demonstrated herein to be linked to diabetes and its complications.

For example, the method may involve determining a level of NSE mRNA in the subject's blood wherein an increase in NSE mRNA (e.g. relative to a healthy control) is indicative of an increased susceptibility to diabetes mellitus. In another embodiment, a decrease in blood NSE mRNA (e.g. relative to a healthy control or a control diabetic subject) is indicative of an increased susceptibility to diabetic neuropathy. In a further embodiment, an increase in blood NSE mRNA (e.g. relative to a control subject with background retinopathy) is indicative of an increased susceptibility to preproliferative retinopathy.

In another embodiment, the biomarker or protein is RPE65. When the protein is RPE65, the condition may be diabetes mellitus or a complication thereof, particularly type 2 diabetes mellitus, especially diabetic retinopathy. Changes in levels of blood RPE65 mRNA are demonstrated herein to be linked to diabetes and its complications.

For example, the method may involve determining a level of RPE65 mRNA in a subject's blood, wherein an increase in RPE65 mRNA (e.g. relative to a healthy control) is indicative of an increased susceptibility to diabetes mellitus. In one embodiment, an increase in RPE65 mRNA (e.g. relative to a healthy control or to a diabetic control without retinopathy) is indicative of increased susceptibility to diabetic retinopathy. In another embodiment, an increase in RPE65 mRNA (e.g. relative to a healthy control, a diabetic control without retinopathy or a diabetic control with pre-proliferative retinopathy) is indicative of increased susceptibility to proliferative retinopathy.

In a further embodiment, an increase in RPE65 mRNA (e.g. relative to a healthy control or a diabetic control without hypoxia) is indicative of an increased susceptibility to a hypoxic disorder, particularly diabetes mellitus with hypoxia, more particularly diabetic retinopathy with hypoxia. In one embodiment, the hypoxic disorder may be sleep apnea, e.g. obstructive sleep apnea (OSA). Thus the condition may be, for example, diabetes mellitus with OSA, including diabetic retinopathy with OSA. More preferably the condition is pre-proliferative or proliferative diabetic retinopathy with OSA.

In another embodiment, the biomarker or protein is retinoschisin. When the protein is retinoschisin, the condition may be diabetes mellitus or a complication thereof, particularly type 2 diabetes mellitus, especially diabetic retinopathy. Changes in levels of blood retinoschisin mRNA are demonstrated herein to be linked to diabetes and its complications.

For example, the method may involve determining a level of retinoschisin mRNA in a subject's blood, wherein an increase in retinoschisin mRNA (e.g. relative to a healthy control) is indicative of an increased susceptibility to diabetes mellitus, particularly diabetes mellitus without retinopathy. In one embodiment, a decrease in retinoschisin mRNA (e.g. relative to a diabetic control without retinopathy) is indicative of diabetes mellitus with retinopathy, e.g. background diabetic retinopathy, preproliferative diabetic retinopathy or proliferative retinopathy.

In a further embodiment, a decrease in retinoschisin mRNA (e.g. relative to a healthy control or a diabetic control without hypoxia) is indicative of an increased susceptibility to a hypoxic disorder, particularly diabetes mellitus with hypoxia, more particularly preproliferative or proliferative diabetic retinopathy with hypoxia. In one embodiment, the hypoxic disorder may be sleep apnea, e.g. obstructive sleep apnea (OSA). Thus the condition may be, for example, preproliferative or proliferative diabetic retinopathy with OSA.

In another embodiment, the biomarker or protein is rhodopsin. When the protein is rhodopsin, the condition is preferably a hypoxic disorder, particularly diabetes mellitus with hypoxia, more particularly diabetic retinopathy with obstructive sleep apnea. For example, the method may involve determining a level of rhodopsin mRNA in a subject's blood, wherein an increase in rhodopsin mRNA (e.g. relative to a normal control or to a diabetic control without hypoxia) is indicative of an increased susceptibility to diabetes mellitus with hypoxia, particularly diabetic retinopathy with obstructive sleep apnea, more particularly preproliferative or proliferative diabetic retinopathy with OSA.

In further embodiments, the method may involve determining a level of two, three or four biomarkers (e.g. mRNAs) selected from NSE, RPE65, retinoschisin and rhodopsin in a subject's blood, wherein a level of the two or more biomarkers or mRNAs is indicative of susceptibility to a condition associated with metabolic syndrome, preferably diabetes mellitus, more preferably diabetic retinopathy, e.g. preproliferative or proliferative retinopathy. In these embodiments, a combination of the above markers is used to determine susceptibility to the condition. Individual mRNAs may be increased or decreased relative to a control level as discussed in the preceding paragraphs.

In a further embodiment, the biomarker or protein is 11β-hydroxysteroid dehydrogenase (11β-HSD). In one embodiment, the protein is 11β-hydroxysteroid dehydrogenase type 1 (11β-HSD1), whereas in an alternative embodiment the protein is 11β-hydroxysteroid dehydrogenase type 2 (11β-HSD2). When the protein is 11β-hydroxysteroid dehydrogenase, the condition is preferably a cardiovascular disorder, e.g. hypertension.

For example, the method may involve determining a level of 11β-hydroxysteroid dehydrogenase type 1 mRNA in a subject's blood, wherein a difference (e.g. an increase or decrease) in 11β-hydroxysteroid dehydrogenase type 1 mRNA (e.g. relative to a healthy control) is indicative of an increased susceptibility to metabolic syndrome.

In another embodiment, the method involves determining a level of 11β-hydroxysteroid dehydrogenase type 2 mRNA in a subject's blood, wherein a decrease in 11β-hydroxysteroid dehydrogenase type 2 mRNA (e.g. relative to a healthy control) is indicative of a disorder associated with metabolic syndrome. Preferably the disorder is hypertension. In this embodiment, the level of 11β-HSD2 mRNA is preferably determined in plasma from the subject's blood, i.e. in cell-free plasma.

In another embodiment, the biomarker or protein is cardiac troponin T (cTnT). In this embodiment, the condition may be, for example, a cardiovascular disorder, preferably congestive heart failure.

For example, the method may involve determining a level of cardiac troponin T in a subject's blood, wherein an increase in cTnT mRNA in the subject's blood (e.g. relative to a healthy control) is indicative of an increased susceptibility to congestive heart failure (CHF). In one embodiment, the level of cTnT mRNA may be indicative of the severity of congestive heart failure. For example an increased level of cTnT mRNA, relative to a mild or moderate CHF control, may be indicative of severe CHF.

In another embodiment, the biomarker is plasma DNA. In this embodiment, a decrease in the level of plasma DNA in the subject's blood (e.g. relative to a healthy control) is indicative of an increased susceptibility to a cardiovascular disorder, particularly hypertension. In one embodiment, the level of plasma DNA is determined by detecting a level of DNA encoding β-globin in the subject's blood.

In a further aspect, the present invention provides a kit for assessing susceptibility to a condition associated with metabolic syndrome in a subject, comprising one or more oligonucleotide primers suitable for determining a level of a nucleic acid representing a biomarker in the subject's blood, wherein the biomarker is selected from the group consisting of plasma DNA, neuron-specific enolase, 11β-hydroxysteroid dehydrogenase, rhodopsin, retinoschisin, RPE65 and cardiac troponin T; and a control sample suitable for indicating a level of the biomarker in blood of a control subject.

In one embodiment, the oligonucleotide primers are suitable for amplifying the nucleic acid by a polymerase chain reaction. Preferably the oligonucleotide primers are suitable for determining a level of the biomarker in the subject's blood by reverse transcriptase polymerase chain reaction.

In one embodiment, the biomarker comprises an mRNA encoding a protein selected from the group consisting of neuron-specific enolase, 11β-hydroxysteroid dehydrogenase, rhodopsin, retinosrchisin, RPE65 and cardiac troponin T.

In one embodiment, the kit comprises at least two pairs of oligonucleotide primers, each pair of oligonucleotide primers being suitable for determining a level of a biomarker in the subject's blood. In further embodiments, the kit may comprise three, four, five or more pairs of primers for amplifying several different biomarkers as defined above.

Embodiments of the present invention advantageously provide methods and kits for detecting conditions associated with metabolic syndrome, enabling their rapid and early detection.

DETAILED DESCRIPTION OF THE INVENTION

Figure 1:
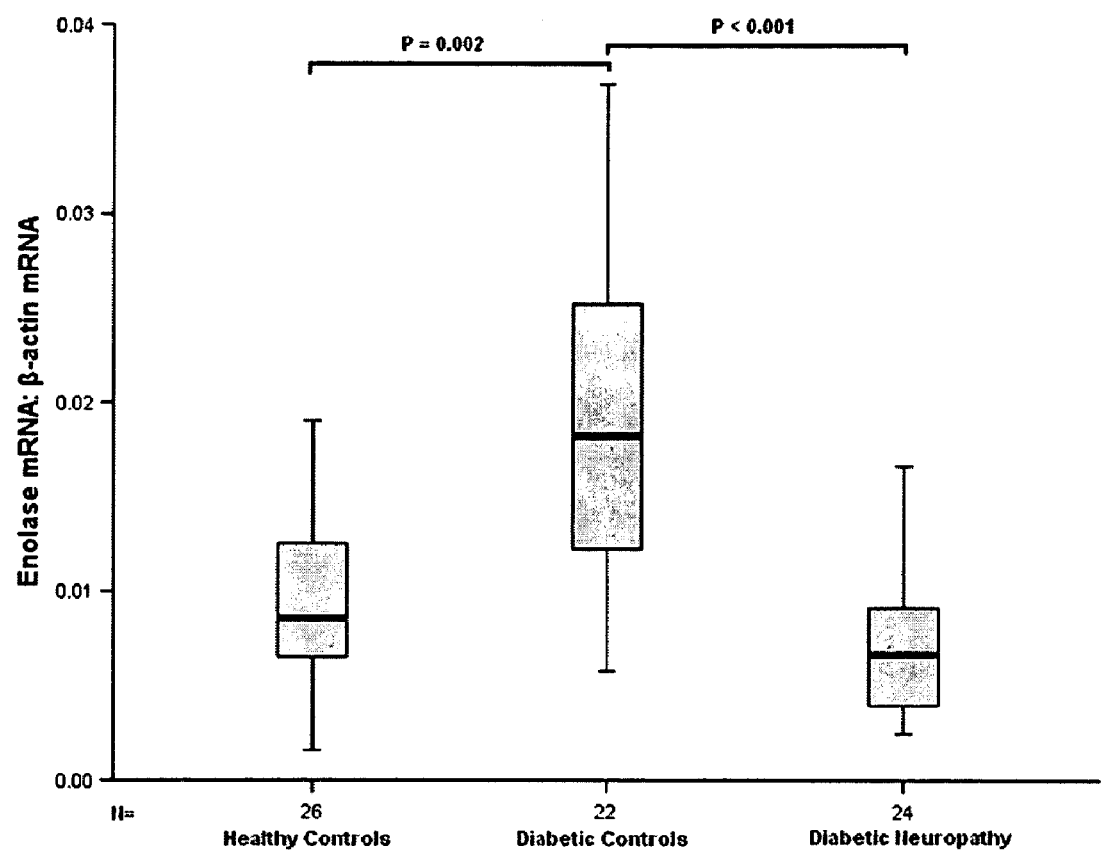
FIG. 1. Circulating enolase mRNA levels in healthy subjects, diabetic patients, and patients with diabetic neuropathy.

The term "blood" as used herein refers to a blood sample or preparation from a subject being tested for susceptibility to a condition associated with metabolic syndrome. The term encompasses whole blood or any fractions of blood, including fractions which are cell free. Examples of blood samples which may be used in the present invention include plasma and serum. A blood sample that is essentially free of cells is also referred to as "acellular", where generally no platelets are present.

Neuron-specific enolase, 11β-hydroxysteroid dehydrogenase, rhodopsin, retinoschisin, RPE65 and cardiac troponin T as used herein, refer to the genes (including their variants and mutants), their polynucleotide transcripts and proteins encoded by these genes. These genes are exemplified by the sequences set forth in publicly-available databases under the accession no.s listed in Table 8. Preferably the genes are human genes and the method is performed in a human, although the method may also be performed in non-human animal species (e.g. in a non-human mammal) where appropriate.

A control level of the mRNA or biomarker may be determined from a single control sample, e.g. from a single normal subject who is known not to suffer from the condition. More preferably, a control level of the mRNA is determined from a mean level in a number of healthy subjects. In certain embodiments, control samples according to the present invention contain a known amount of the mRNA encoding a particular protein that closely reflects the average level of such mRNA in a control subject, e.g. a normal healthy individual.

An increase or a decrease in the level of mRNA from the control as used herein refers to a positive or negative change in amount from the control. An increase is preferably at least 25%, more preferably at least 50%, more preferably at least 75% and most preferably at least 100%. Similarly, a decrease is preferably at least 25%, more preferably at least 50%, and most preferably at least 75%.

In one embodiment, the level of a biomarker mRNA in a sample may be detected by a polynucleotide hybridization method. A polynucleotide hybridization method refers to a method for detecting the presence and/or quantity of a polynucleotide based on its ability to form Watson-Crick base-pairing, under appropriate hybridization conditions, with a polynucleotide probe of a known sequence. Examples of such hybridization methods include Southern blotting and Northern blotting.

In a preferred embodiment, the level of biomarker mRNA may be detected by a reverse transcriptase polymerase chain reaction method. The level of plasma DNA may be detected by PCR. Oligonucleotide primers suitable for use in the present invention include those that can be used in a polymerase chain reaction (PCR) to amplify a nucleotide sequence (e.g. a cDNA sequence) originated from an mRNA encoding a protein of interest, such as neuron-specific enolase, 11β-hydroxysteroid dehydrogenase, rhodopsin, retinoschisin, RPE65 and cardiac troponin T. Preferably at least one of the PCR primers for amplification of a nucleotide sequence encoding an above-named protein is sequence-specific for the protein. Primers for use in RT-PCR methods are preferably intron-spanning where appropriate, in order to avoid amplification of genomic DNA. Suitable primers for use in RT-PCR amplification of the above biomarkers, as well as for quantitation of plasma DNA (based on amplification of a β-globin sequence) are given in Table 8.

In particular embodiments, the amount of biomarker mRNA in a blood sample is quantitatively determined, preferably following an amplification procedure, e.g. reverse transcriptase polymerase chain reaction (RT-PCR). The level of one of more of the above-named mRNAs is then compared to a standard control. An increase or decrease in the mRNA level indicates the presence of or an increased risk of developing the disorder.

In one embodiment, the first step is to obtain a blood sample from a subject to be tested. Collection of blood from a subject is performed in accordance with a standard protocol used clinically. An appropriate amount of peripheral blood, e.g. between 5-20 ml, is collected and may be stored according to standard procedure prior to further preparation.

Whole blood, or alternatively serum or plasma, are suitable for use in the present invention and can be obtained by well known methods. For example, a subjects blood can be placed in a tube containing EDTA or a specialized commercial product such as Vacutainer SST (Becton Dickinson, Franklin Lakes, N.J.) to prevent blood clotting, and plasma can then be obtained from whole blood through centrifugation. On the other hand, serum is obtained through centrifugation following blood clotting. Centrifugation is typically conducted at an appropriate speed, e.g. 1,500-3,000×g, in a chilled environment, e.g., at a temperature of about 4-10° C. Plasma or serum may be subject to additional centrifugation steps before being transferred to a fresh tube for RNA extraction.

There are numerous methods for extracting mRNA from a biological sample. The general methods of mRNA preparation (e.g. described by Sambrook and Russell, Molecular Cloning: A Laboratory Manual 3d ed., 2001) can be followed. Various commercially available reagents or kits, such as PAXgene Blood RNA Tubes (Qiagen, Valencia, Calif.), Trizol reagent (Invitrogen, Carlsbad, Calif.), Oligotex Direct mRNA Kits, RNeasy Mini Kits (Qiagen, Hilden, Germany), and PolyATtract Series 9600™ (Promega, Madison, Wis.), may also be used to obtain mRNA from a blood sample. Combinations of more than one of these methods may also be used.

It is essential that all contaminating DNA be eliminated from the RNA preparations. Thus, careful handling of the samples, thorough treatment with DNase, and proper negative controls in the amplification and quantification steps should be used.

Once mRNA is extracted from a blood sample, the amount of mRNA encoding a protein of interest may be quantified. The preferred method for determining the mRNA level is an amplification-based method, e.g. by PCR. Particularly preferred is a real-time quantitative PCR method.

Prior to the amplification step, a DNA copy (cDNA) of the mRNA of interest must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbarf in Diagnostic Molecular Biology: Principles and Applications pp. 401-406; Persing et al., eds., Mayo Foundation, Rochester, Minn., 1993; Egger et al., J. Clin. Microbiol. 33: 1442-1447, 1995; and U.S. Pat. No. 5,075,212.

The general methods of PCR are well known in the art and are thus not described in detail herein. For a review of PCR methods protocols, and principles in designing primers, see e.g. Innis, et al. PCR Protocols: A Guide to Methods and Applications, Academic Press, Inc. N.Y. 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

PCR amplification of a cDNA derived from the target mRNA is typically used in practicing the present invention. One of skill in the art will recognize, however, that amplification of these mRNA species in a blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of mRNA markers in blood. For a review of branched-DNA signal amplification for direct quantitation of nucleic acid sequences in clinical samples, see Nolte, Adv. Clin. Chem. 33: 201-235, 1998.

The mRNA of interest can also be detected using other standard techniques, well known to those of skill in the art. Although the detection step is typically preceded by an amplification step, amplification is not required in the methods of the invention. For instance, the mRNA may be identified by size fractionation (e.g. gel electrophoresis), whether or not proceeded by an amplification step. After running a sample in an agarose or polyacrylamide gel and labeling with ethidium bromide according to well known techniques (see, Sambrook and Russell, supra), the presence of a band of the same size as the standard control is an indication of the presence of a target mRNA, the amount of which may then be compared to the control based on the intensity of the band.

Alternatively, oligonucleotide probes specific to mRNA encoding a biomarker protein can be used to detect the presence of such mRNA species and indicate the amount of mRNA in comparison to the standard control, based on the intensity of signal imparted by the probe.

Sequence-specific probe hybridization is a well known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats are well known in the art, including but not limited to, solution phase, solid phase, or mixed phase hybridization assays. The following articles provide an overview of the various hybridization assay formats: Singer et al., Biotechniques 4: 230, 1986; Haase et al., Methods in Virology, pp. 189-226, 1984; Wilkinson, In situ Hybridization, Wilkinson ed., IRL Press, Oxford University Press, Oxford; and Hames and Higgins eds., Nucleic Acid Hybridization: A Practical Approach, IRL Press, 1987.

The hybridization complexes are detected according to well known techniques and the detection is not a critical aspect of the present invention. Nucleic acid probes capable of specifically hybridizing to a target nucleic acid, i.e. the mRNA or the amplified DNA, can be labeled by any one of several methods typically used to detect the presence of hybridized nucleic acids. One common method of detection is the use of autoradiography using probes labeled with $^{3}H$, $^{125}I$, $^{35}S$, $^{14}C$, or $^{32}P$, or the like. The choice of radioactive isotope depends on research preferences due to ease of synthesis, stability, and half lives of the selected isotopes.

Other labels include compounds (e.g., biotin and digoxigenin), which bind to antiligands or antibodies labeled with fluorophores, chemiluminescent agents, and enzymes.

Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, Tetrahedron Letts., 22: 1859-1862, 1981, using an automated synthesizer, as described in Needham-VanDevanter et al., Nucleic Acids Res. 12; 6159-6168, 1984. Purification of oligonucleotides is by either native acrylamide gel electrophoresis or by anion-exchange HPLC as described in Pearson and Regnier, J. Chrom., 255: 137-149, 1983.

In order to establish a control level of each biomarker, a normal group of subjects may be selected. Their healthy status (e.g. absence of the condition to be tested for) may be confirmed, if required, by standard tests appropriate to the particular condition, e.g. blood glucose monitoring or blood pressure determination. Preferably the size of the control group is sufficiently large such that the average amount of mRNA encoding a biomarker calculated from the group can be reasonably regarded as representative of the normal or average amount among the general population.

Once an average value is established for the amount of mRNA encoding any one protein based on the individual values found in each subject of the selected group, this values is considered a standard for the mRNA. Any blood sample that contains a similar amount of mRNA can thus be used as a standard control. A solution containing mRNA encoding neuron-specific enolase, 11β-hydroxysteroid dehydrogenase, rhodopsin, retinoschisin, RPE65 or cardiac troponin T with a concentration of the established average of the same species can also be artificially assembled and serve as a standard control.

In further embodiments, the method involves detection of the biomarker at the protein level. For example, methods for detecting proteins may include the use of an antibody, capture molecule, receptor, or fragment thereof which selectively binds to the protein. Antibodies which bind to the biomarkers described herein are known or may be produced by methods known in the art, including immunization of an animal and collection of serum (to produce polyclonal antibodies) or spleen cells (to produce hybridomas by fusion with immortalised cell lines leading to monoclonal antibodies). Detection molecules such as antibodies may optionally be bound to a solid support such as, for example, a plastic surface or beads or in an array. Suitable test formats for detecting protein levels include, but are not limited to, an immunoassay such as an enzyme-linked immunosorbent assay (ELISA), radioimmunoassay (RIA), Western blotting and immunoprecipitation.

Alternatively the level of the biomarker protein may be determined by mass spectroscopy. Mass spectroscopy allows detection and quantification of a cytokine protein by virtue of its molecular weight. Any suitable ionization method in the field of mass spectroscopy known in the art can be employed, including but not limited to electron impact (EI), chemical ionization (CI), field ionization (FDI), electrospray ionization (ESI), laser desorption ionization (LDI), matrix assisted laser desorption ionization (MALDI) and surface enhanced laser desorption ionization (SELDI). Any suitable mass spectrometry detection method may be employed, for example quadrapole mass spectroscopy (QMS), fourier transform mass spectroscopy (FT-MS) and time-of-flight mass spectroscopy (TOF-MS).

As described above, in some embodiments kits according to the present invention may comprise one or more pairs of oligonucleotide primers for amplifying biomarkers and a control sample. In addition, such kits may optionally further comprise one or more additional components, particularly reagents for performing RT-PCR methods. For instance, the kits may comprise reagents for RNA extraction, reverse transcription (e.g. a reverse transcriptase) or PCR (for example labelled primers, deoxynucleotides, a thermostable (e.g. Taq) polymerase etc.) as well as buffers suitable for performing any of these steps. The kits may farther comprise vials, containers and other packaging materials for storing the above reagents, as well as instructions for performing a method as defined herein.

The following examples are provided by way of illustration only and not by way of limitation. Those of skill in the art will readily recognize a variety of non-critical parameters that could be changed or modified to yield essentially similar results.

EXAMPLES

Example 1

Measurement of Circulating Neuron-Specific Enolase mRNA in Diabetes Mellitus

Summary

In this study we measured the levels of neuron-specific enolase mRNA as a possible marker of diabetic neuropathy. Blood samples were collected from healthy controls (n=26), diabetic controls (no known neuropathy or retinopathy) (n=22), and diabetics with clinically diagnosed neuropathy (n=24) into PAXgene blood RNA tubes. mRNA was extracted, reverse-transcribed to cDNA, and measured by real-time quantitative PCR. Enolase mRNA levels were normalized by the simultaneous measurement of $\beta$-actin mRNA. The results showed that the enolase mRNA was significantly (P=0.002) higher in the diabetic control (median=0.018; range=0.006-0.037) group compared to healthy subjects (median=0.0086; range=0.0016-0.039). However, the diabetic neuropathy group showed lower enolase levels (median=0.0067; range=0.0025-0.017) compared to both healthy subjects (P=0.06) and diabetic controls (P<0.001). In the diabetic neuropathy group patients with preproliferative (median=0.0095; range=0.0031-0.0167) or proliferative retinopathy (median=0.011; range=0.006-0.014) had significantly (P=0.001) higher enolase mRNA compared to patients with background retinopathy (media=0.0044; range=0.0025-0.0099). It is concluded that levels of enolase mRNA are decreased in diabetic neuropathy and this molecular marker is useful in differentiating early from advanced eye disease in those diabetics diagnosed with neuropathy.

Introduction

Retinopathy, neuropathy, and nephropathy are common complications in patients with diabetes mellitus. The potential value of circulating nucleic acids in plasma and serum (CNAPS) has been demonstrated in diabetic retinopathy and nephropathy (1).

The estimates of the prevalence of diabetic neuropathy (DN), which is a heterogenous disorder, vary depending on the diagnostic criteria (2). The prevalence of DN after 25 years was 45% (3). Diabetic neuropathy accounts for 50% to 75% of nontraumatic amputations (4,5) and is linked to poor quality of life and heavy economic burden (6,7).

Although a range of diagnostic tools are available, underdiagnosis or misdiagnosis remain a problem in clinical practice. The GOAL A1C study, evaluating 7000 patients, reported detection of only 38% with mild and 61% with severe neuropathy. The importance of timely diagnosis is stressed by the fact that allocation of suitable interventions in high-risk patients with diabetes has been shown to decrease the rate of ulceration and amputation (8). We postulated that in diabetic neuropathy neuron-specific nucleic acids may appear in the circulation and these may form a blood test for the early detection of this disorder.

The marker proposed was neuron-specific enolase (NSE), which is a highly soluble intracellular protein principally located in neuronal cytoplasm and in neuroendocrine cells (9,10). The gene for NSE has been mapped to human chromosome 12. NSE is readily secreted into the cerebrospinal fluid (CSF) and blood after tissue injury, and has been shown to have a biological half-life of 48 hours (11-13). The aim of this study was to demonstrate the value of circulatory NSE mRNA levels in detecting diabetic neuropathy.

Materials and Methods

Ethical approval was granted by the Guy's and St Thomas' Research Ethics Committee. Patients were recruited from the Diabetic Foot Clinic at St Thomas' Hospital from January to March 2006. Patients with type 1 or type 2 diabetes and clinically overt signs of any of the diabetic neuropathy syndromes were recruited. All of the patients presenting in the diabetic foot clinic had distal symmetric polyneuropathy (DPN). The great majority of patients attending this clinic have long-standing DN and were undergoing routine examination of their feet. Blood samples were taken from all subjects into two PAXgene™ Blood RNA Tubes (2.5 mL) and then stored at −80° C. until analysis.

Whole blood RNA was extracted using the PAXgene Blood RNA Kit, including treatment with DNAse I to prevent genomic DNA contamination, strictly following manufacturer's instruction (QIAgen). Extracted RNA was stored at −80° C. until required for cDNA synthesis. Reverse transcription was carried out using SuperScript II™ reverse transcriptase following the manufacturer's instructions (Invitrogen Life Sciences, Scotland). The cDNA generated was stored at −80° C. until required for quantitation. Separately, samples were also subjected to the above procedure with the exception that SuperScript II was replaced with water (negative control).

The ABI 7000 Sequence Detection System (PE Applied Biosystems) was used to amplify cDNA and detect PCR products using sequence-specific oligonucleotide probes and intron-spanning specific primers. β-actin cDNA was amplified using the Pre-Developed Assay Reagents Taqman_assay (PE Applied Biosystems). In the case of the enolase Taqman assays, 900 nM forward and reverse primers, 250 nM probe, X2 Taqman Universal Master Mix (25 µL), and cDNA sample (10 µL) were present in each reaction. For all assays, standards and samples were analyzed in duplicate in a final reaction volume of 50 µL. Standard curves were prepared from serial dilutions of cDNA (Clontech) obtained from normal healthy human brain. A waterblank was also incorporated in each run for the respective assays. All enolase mRNA assays were run simultaneously with β-actin on 96-well optical reaction plates. PCR amplification included an initial phase of 2 min at 50° C., followed by 10 min at 95° C., then 40 cycles of 15 seconds at 95° C. and 1 min at 60° C.

Total RNA was quantitated by diluting 20 µL of the 80 µL RNA extract in 380 µL of 10 mM Tris-Cl, pH 7.5, and measuring the absorbance at 260 nm in a spectrophotometer (Pharmacia GeneQuant RNA/DNA Calculator). Patient characteristics were analyzed using one-way ANOVA (analysis of variance) and where necessary a post-hoc test was carried out. Experimental results were analyzed with the Mann-Whitney U-test for nonparametric data. Significance was defined as $P<0.05$.

Results

In total 72 individuals consisting of 26 healthy subjects and 46 diabetic patients, of whom 24 were diagnosed with diabetic neuropathy, were recruited. Of the 24, all but one were diagnosed with diabetic retinopathy (Table 1). Body mass index (BMI) was significantly higher in patients with DN compared to healthy subjects. The duration of diabetes was significantly longer (P<0.001) and HbA1c was significantly higher in patients with DN compared to diabetic controls.

TABLE 1

Characteristics of Healthy Subjects and Diabetic Patients with and without Neuropathy

|  | Healthy Controls a | Diabetic Controls b | Diabetic Neuropathy c |
|---|---|---|---|
| n | 26 | 22 | 24 |
| Age (years) | 44.2 ± 17.4 | 55.2 ± 12.4 | 59.6 ± 12.3 |
| BMI (kg/m2) | 24.5 ± 4.0c | 32.7 ± 6.1 | 31 ± 6.8a |
| Sex (M/F) | 18/8 | 17/5 | 18/6 |
| Duration of diabetes (years) | — | 3.75 ± 4.2c | 18.1 ± 13.1b |
| Random blood glucose (mmol/L) | — | 8.1 ± 2.6 | 9.5 ± 4.5 |
| HbA1c (%) | — | 6.6 ± 0.87c | 8.2 ± 2.0b |
| ACR (mg/mmol) | — | 1.5 ± 1.72 | 8.2 ± 16.0 |
| Plasma creatinine (µmol/L) | — | 88.8 ± 25.3 | 109 ± 50.0 |
| Systolic blood pressure (mmHg) | — | — | 139.7 ± 20.0 |
| Diastolic blood pressure (mmHg) | — | — | 73.4 ± 12.5 |
| WBC count (×10⁶/mL) | — | 7.7 ± 2.9 | 6.7 ± 2.0 |

NOTE:
Italic letters denote significant difference (P < 0.05) with corresponding group where a = healthy controls; b = diabetic controls; and c = diabetic neuropathy.
BMI = body mass index;
HbA1c = glycosylated haemoglobin;
ACR = urinary albumin: creatinine ratio;
WBC = white cell count.

There was a 100% detection rate of the markers investigated—enolase and β-actin.

Precision for RNA extraction from whole blood was estimated by collecting 20 samples of blood from one individual, extracting the RNA, and measuring the total RNA by spectrophotometric analysis. The mean concentration of extracted RNA was 11.7±0.49 µg/mL with a coefficient of variation (CV) of 8.9%.

The analytical procedure of the entire protocol was determined by carrying out real-time RT-PCR on the 20 extracted blood samples from one individual using enolase and β-actin for quantification. The CVs were calculated from the raw Ct values for each marker and found to be between 1-2% in all cases.

Diabetic controls had significantly higher levels of circulating enolase mRNA than did healthy subjects (P=0.002). Patients with diabetic neuropathy had significantly lower levels of enolase (P<0.001) relative to diabetic controls (FIG. 1). There was no significant difference between the healthy and diabetic neuropathy cohort.

Figure 2:
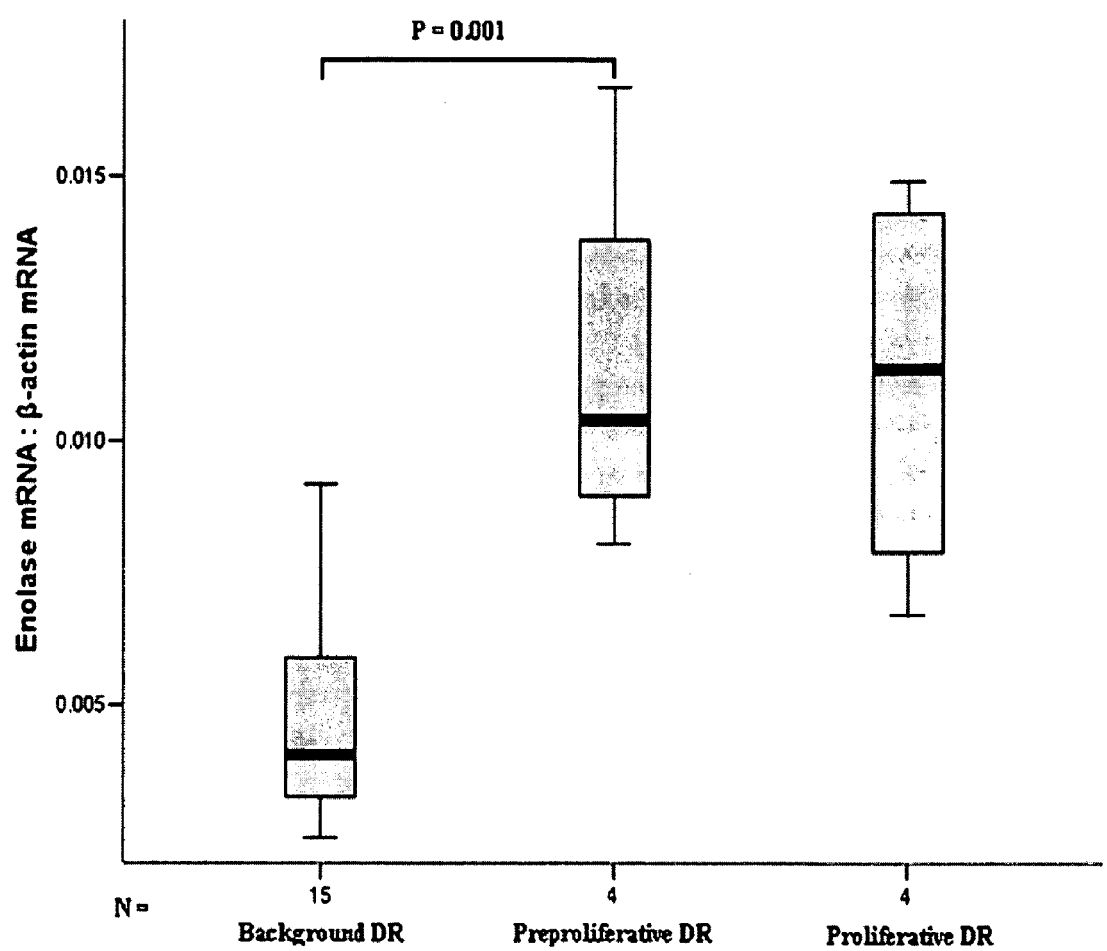
FIG. 2. Circulating enolase mRNA levels in patients with diabetic retinopathy and neuropathy.

When the diabetic neuropathy patients were examined according to their eye status, patients with preproliferative retinopathy had significantly higher levels of circulating enolase mRNA compared to those with background retinopathy (P=0.001) (FIG. 2).

Discussion

During the past few years, a number of studies have pointed to raised circulating nucleic acid concentrations in pathologic processes, including cancer (14), stroke (15), trauma (16) and nephropathy (1). We have extended these observations to the study of diabetic neuropathy. Neuron-specific enolase mRNA was detected and quantified in the circulation of all healthy controls as well as diabetic patients.

Neuron-specific enolase is an intracellular protein that is predominantly present in neuronal cytoplasm as well as central and peripheral neuroendocrine cells. NSE has a biological half life of 48 hours and is constantly being used to maintain excitability of the neuronal membrane (11) and therefore mRNA coding for the protein must constantly be transcribed. Furthermore, NSE has been found to be present within plasma and CSF in small concentrations in physiological conditions (17). The release of mRNA within healthy individuals may therefore be a result of controlled secretion by the neurons.

Circulating NSE mRNA levels were significantly higher in diabetic controls relative to healthy controls (P=0.002). As NSE has been shown to be readily released into CSF and blood after tissue injury, this finding suggests that hyperglycemic insult, even before clinical manifestation of DN, leads to increased release of NSE mRNA into the circulation.

Comparison of the diabetic neuropathy group with the diabetic controls showed a significant reduction of circulating NSE mRNA levels (P<0.001). Furthermore, there was also an indication that levels were lower in the DN group relative to the healthy cohort (P=0.06). It is conceivable that the persistent hyperglycemic insult in the years before the diagnosis of DN could lead to an inability of the neurons to transcribe NSE mRNA at previous levels. This may be due to the severe and widespread damage of the neuronal network among DN patients leading to the reduction of intracellular regions capable of transcribing NSE mRNA.

Patients presenting with DN were categorized into their respective groups with regards to DR status. The circulating NSE mRNA levels were shown to be significantly higher in preproliferative DR patients than those with background DR(P=0.001) despite the low patient numbers in the former set of patients. This was a rather interesting finding given that diabetic retinopathy is known to lead to ischemic changes in the inner retina, resulting in atrophy of the neuronal layer. Extensive loss of retinal neurons may lead to release of NSE mRNA into the circulation, which may rise with increasing severity of DR. However, there was no significant difference between the background and proliferative DR groups. This may be ascribed to the widespread damage in the retinal neuronal layer in the proliferative DR stage, thus reducing the capacity, both numerically and metabolically, to transcribe increased levels of NSE mRNA.

In this study we have investigated the potential of NSE mRNA as a marker for diabetic neuropathy. We conclude that circulating NSE mRNA can be detected and quantified in healthy subjects and diabetic patients and that this provides the basis for a blood test to detect diabetic neuropathy.

REFERENCES

1. Butt A. N. et al. 2006. Circulating nucleic acids and diabetic complications. *Ann. N. Y. Acad. Sci.* 1075: 258-270.
2. Gooch, C. & D. Podwall. 2004. The diabetic neuropathies. *Neurologist* 10: 311-322.
3. Pirart, J. 1977. Diabetes mellitus and its degenerative complications: a prospective study of 4400 patients observed between 1947 and 1973 (third and last part). *Diabetes Metab.* 3: 245-256.
4. Caputo, G. M. et at 1994. Assessment and management of foot disease in patients with diabetes. *N. Engl. J. Med.* 331: 854-860.
5. Holzer, S. E. et al. 1998. Costs and duration of care for lower extremity ulcers in patients with diabetes. *Clin. Ther.* 20: 169-181.
6. Ollendorf, D. A. et al. 1998. Potential economic benefits of lower-extremity amputation prevention strategies in diabetes. *Diabetes Care* 21: 1240-1245.
7. Ramsey, S. D. et al. 1999. Incidence, outcomes, and cost of foot ulcers in patients with diabetes. *Diabetes Care* 22: 382-387.
8. Rith-Najarian, S. et al. 1998. Reducing lower extremity amputations due to diabetes: application of the staged diabetes management approach in a primary care setting. *J. Fam. Pract.* 47: 127-132.
9. Marangos, P. J. et al. 1979. Measurement of neuronspecific (NSE) and non-neuronal (NNE) isoenzymes of enolase in rat, monkey and human nervous tissue. *J Neurochem.* 33: 319-329.
10. Kato, K. et al. 1982, Distribution of nervous system specific forms of enolase in peripheral tissues. *Brain Res.* 237: 441-448.
11. Kaiser, E. et al. 1989. Clinical biochemistry of neuron specific enolase. *Clin. Chim. Acta* 183: 13-31.
12. Marangos, P. J. & D. E. Schmechel. 1987. Neuron specific enolase a clinically useful marker for neurons Annals of the New York Academy of Sciences and neuroendocrine cells. *Annu. Rev. Neurosci.* 10: 269-295.
13. Ishiguro, Y. et al. 1983. Nervous system-specific enolase in serum as a marker for neuroblastoma. *Pediatrics* 72: 696-700.
14. Stroun, M. et al. 1989. Neoplastic characteristics of the DNA found in the plasma of cancer patients. *Oncology* 46: 318-322.
15. Rainer, T. H. et al. 2003. Prognostic use of circulating plasma nucleic acid concentrations in patients with acute stroke. *Clin. Chem.* 49: 562-569.
16. Lo, Y. M. et al. 2000. Plasma DNA as a prognostic marker in trauma patients. *Clin. Chem.* 46; 319-323.
17. Schmechel, D. et al. 1978. Brain enolases as specific marker of neuronal and glial cells. *Science* 199: 313 315.

Example 2

Retina-Specific mRNA in the Assessment of Diabetic Retinopathy

Summary

In the present study we investigated three retina-specific markers in blood to determine their suitability as markers of diabetic retinopathy (DR). The markers were RPE65, retinoschisin, and melanopsin. Whole blood was collected from diabetic patients and healthy controls into PAXgene Blood RNA tubes and RNA was extracted using the PAXgene Blood RNA System. Quantitative real-time PCR was used to quantify mRNA for RPE65, retinoschisin, and melanopsin. β-actin mRNA was used for normalization. RPE65, retinoschisin, and β-actin mRNA were detected in 100% of subjects; melanopsin was not detected in either controls or diabetic patients. Circulating RPE65mRNA concentration was 63% higher in diabetic patients than in healthy individuals (P=0.019), whereas retinoschisin showed no change between the two groups. Compared with healthy controls, circulating RPE65 mRNA concentration was higher in diabetics with no retinopathy (30%; P=NS), background DR (93%; P=0.01), preproliferative DR (20%; P=NS), and proliferative DR (107%; P=0.004). Compared with diabetics with no retinopathy, levels of RPE65 mRNA were also significantly higher (60%) in the presence of proliferative DR (P=0.029). In contrast, levels of retinoschisin mRNA were lower in background DR (34%; P=0.033), preproliferative DR (43%; P=0.026), and proliferative DR (47%; P=0.038) compared to that in diabetics without retinopathy. We conclude that not all retina-specific mRNA species are detectable in circulation (e.g., melanopsin). This may be related to differences in expression levels for the individual markers. Both RPE65 and retinoschisin were detectable and demonstrated contrasting trends in diabetics with and without retinopathy. In combination with rhodopsin, RPE65, and retinoschisin, mRNA provide a useful blood test for DR.

Introduction

Retinopathy is a common microvascular complication of diabetes mellitus (1). Diagnosis and assessment of this eye disorder necessitates the requirement for lengthy and costly clinical procedures and involvement of specialist health professionals (2). With the incidence of diabetes, and therefore retinopathy, rising globally, a simple and objective blood test for the assessment of eye status would be highly desirable. Rhodopsin mRNA is present in the peripheral blood of diabetic patients with and without retinopathy and healthy controls. Diabetics showed significantly higher levels of rhodopsin mRNA compared with healthy subjects (3). A trend was also observed with rhodopsin mRNA levels increasing with severity of diabetic retinopathy. In the present study we have analyzed mRNA for the following retina-specific proteins: RPE65, retinoschisin, and melanopsin. These proteins are found in different regions of the retina and have distinctly different roles in retinal function and integrity. Unlike rhodopsin, these proteins are not known to be found in the rod cells of the retina and are not thought to be directly involved with the visual imaging process.

RPE65 is the major protein of the microsomal membranes in the retinal pigment epithelium (4). Retinoschisin is generally thought to function as a cell adhesion protein that plays a crucial role in maintaining the structural integrity of the retina (5). Recent expression studies of melanopsin have provided compelling evidence that melanopsin is the photopigment of the photosensitive retinal ganglion cells (6).

Materials and Methods

Diabetic subjects were recruited from the diabetes clinic at St Thomas' Hospital, London, and comprised individuals with a confirmed history of diabetes with or without retinopathy. The protocol for this study was approved by St Thomas' Hospital local Research Ethics Committee. This allowed blood sampling and access to the patients' medical notes. The eye status of recruits was determined from the medical notes, and independent examination of fundoscopic photographs. All diabetic patients were allocated into one of four groups: (i) diabetic without retinopathy (diabetic controls); (ii) diabetic with background retinopathy; (iii) diabetic with preproliferative retinopathy; and (iv) diabetic with proliferative retinopathy. Informed consent was obtained from each patient prior to blood collection. Blood samples were also collected from healthy volunteers (n=20) with no known disease, after obtaining informed consent. Peripheral vein blood (2.5 mL) was drawn directly into PAXgene™ Blood RNA Tubes specially designed for the collection and stabilisation of RNA from whole blood (Becton Dickinson). Whole blood RNA was extracted using the PAXgene Blood RNA Kit, including treatment with DNAse I to prevent genomic DNA contamination, strictly following manufacturer's instruction (QIAgen). Extracted RNA was stored at −80° C. until required for cDNA synthesis. Reverse transcription was carried out using SuperScript II™ reverse transcriptase following the manufacturer's instructions (Invitrogen Life Sciences, Scotland). The cDNA generated was stored at −80° C. until required for quantification. Separately, samples were also subjected to the above procedure with the exception that Super-Script II™ was replaced with water (negative control).

The ABI 7000 Sequence Detection System (PE Applied Biosystems) was used to amplify cDNA and detect PCR products using sequence-specific oligonucleotide probes and intron-spanning specific primers. β-actin cDNA was amplified using the pre-developed assay reagents Taqman assay (PE Applied Biosystems). In the case of the RPE65, retinoschisin, and melanopsin Taqman assays, 900 nM forward and reverse primer, 250 nM probe, X2 Taqman Universal Master Mix (25 μL), and cDNA sample (10 μL) were present in each reaction. For all assays, standards and samples were analyzed in duplicate in a final reaction volume of 50 μL. Standard curves were prepared from serial dilutions of cDNA (Clontech) obtained from normal healthy human retina. A water blank was also incorporated in each run for the respective assays. All retina-specific marker assays were run simultaneously with β-actin on 96-well optical reaction plates. PCR amplification included an initial phase of 2 min at 50° C., followed by 10 min at 95° C., then 40 cycles of 15 seconds at 95° C., and 1 min at 60° C. Statistical analysis was performed using SPSS 10. Differences in the measured expression of retina-specific mRNA between healthy individuals and diabetic patient groups were analyzed by Mann-Whitney U-test. A P value of less than 0.05 was considered statistically significant.

Results

Figure 3:
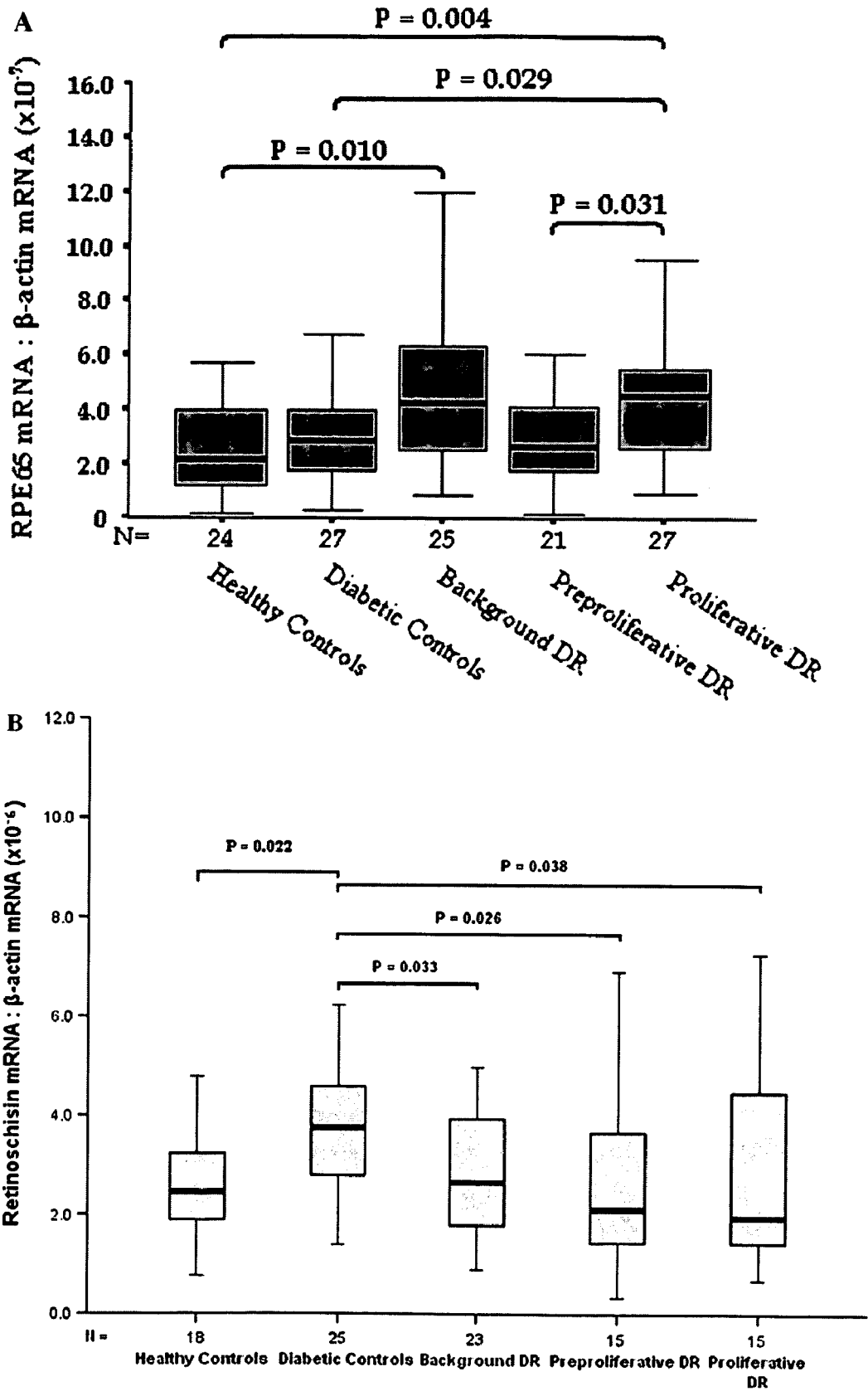
FIG. 3. (A) RPE65 and (B) retinoschisin mRNA levels in healthy controls and diabetic patients with and without retinopathy.

RPE65 and retinoschisin mRNA was detected in the peripheral blood of all healthy and diabetic subjects in this study. Melanopsin was not detected in the circulation of either the healthy controls or patients. FIGS. 3A and 3B summarize the RPE65 and retinoschisin mRNA levels observed in the healthy subjects and all diabetics analyzed. Although not statistically significant, diabetics without retinopathy demonstrated higher median RPE65 mRNA levels compared to healthy controls. A significant difference in RPE65 mRNA was noted between healthy subjects and diabetics with background (P=0.029) and proliferative (P=0.004) retinopathy, respectively. The proliferative retinopathy group of diabetics also had significantly higher RPE65 RNA levels than the diabetics without retinopathy and preproliferative retinopathy. Diabetic patients with proliferative retinopathy showed no change in RPE65 mRNA when compared with levels seen in patients with background retinopathy.

Retinoschisin mRNA in diabetics without retinopathy was significantly higher than levels seen in the healthy controls (P=0.022). There was a downward trend in circulating retinoschisin mRNA levels in the diabetic patients. A comparison of diabetics without retinopathy (diabetic controls) and diabetics with retinopathy showed significantly lower levels of retinoschisin mRNA in background (P=0.033), preproliferative (P=0.026), and proliferative (P=0.038) groups.

Discussion

Rhodopsin mRNA is present in the circulation and its levels correlate with the severity of diabetic retinopathy (3). In the present study we investigated the following retina-specific markers: RPE65, retinoschisin, and melanopsin. The results showed that mRNA for RPE65 and retinoschisin was present in quantifiable amounts in both healthy subjects and patients with and without diabetic retinopathy. In the case of RPE65, and with the exception of the group with preproliferative retinopathy, there was a trend for the relative amounts of RPE65 mRNA detected to increase with severity of retinopathy. This upward trend may be related to the more severe damage, and widespread retinal pathology associated with the progressive stages of diabetic retinopathy. While the precise mechanisms are unclear, it is plausible that the underlying reasons for the increase in RPE65 mRNA observed in peripheral blood may be ascribed to (1) release from dead or dying retinal cells from ischemia, (2) possible upregulation of RPE65 transcription, or (3) controlled secretion of RPE65 mRNA.

These explanations would seem to be in direct contradiction when the argument is applied to retinoschisin mRNA levels. Here an inverse relationship appears to exist, that is, a downward trend was observed, with retinoschisisn mRNA levels decreasing with increase in severity of retinopathy grade. By inference, it would appear that retinoschisin expression is downregulated in response to local retinal insult.

In contrast to RPE65 and retinoschisin, melanopsin mRNA was not detected in the circulation. Melanopsin is known to mediate "nonimaging" photoreceptive tasks such as those involving the circadian rhythms. In the retina, expression of this retinal ganglion-specific photopigment is thought to be diurnal, with highest levels peaking at night (7). In the present study blood was taken from all recruits during daylight hours, which may be the reason we did not see any detectable levels. It would be interesting to analyze nocturnal (during sleep) and daytime blood samples for melanopsin mRNA to see if this theory holds true.

Conclusion

Real-time quantitative PCR measurement of circulating RPE65 retinoschisin, and melanopsin mRNA demonstrated differential expression of these retina-specific markers. In combination with rhodopsin mRNA in peripheral blood, these markers provide a useful, sensitive, and specific blood test for diabetic retinopathy.

REFERENCES

1 Knott, R. et al. 2003. Diabetic eye disease. In *Textbook of Diabetes*, Vol. 48, 3rd ed. J. Pickup & G. Williams, Eds.: 1-48. Blackwell Publishing. Oxford.
2. Vijan, S. et al. 2000. Cost-utility analysis of screening intervals for diabetic retinopathy in patients with type 2 diabetes mellitus. *JAMA* 283: 889-896.
3. Hamaoui, K. et al. 2004. Concentration of circulating rhodopsin mRNA in diabetic retinopathy. *Clin. Chem.* 50: 2152-2155.
4. Wolf, G. 2005. Function of the protein RPE65 in the visual cycle. *Nutr. Rev.* 63: 97-100. 5. Molday, R. S. 2007. Focus on molecules: retinoschisin (RS1). *Exp. Eye Res.* 84: 227-228.
6. Peirson, S. & R. G. Foster. 2006. Melanopsin: another way of signaling light. *Neuron* 49: 331-339.
7. Hannibal, J. 2006. Regulation of melanopsin expression. *Chronobiol. Int.* 23: 159-166.

Example 3

Effect of Hypoxia on Circulating Levels of Retina-Specific Messenger RNA in Type 2 Diabetes Mellitus

Summary

Circulating rhodopsin mRNA levels are higher in diabetic retinopathy (DR). Recent evidence suggests that hypoxia may also be associated with DR. The aim of this study was to investigate the effect of oxygen desaturation on circulating retina-specific mRNA in type 2 diabetic patients. Thirty-five type 2 diabetic patients underwent overnight oximetry. Two parameters from oximetry were used to measure oxygen desaturation: the number of times per hour the oxygen saturation decreased by 4% or greater (number of dips/hr) and percentage of sleep time with oxygen saturation (SpO2) <90%. Blood samples were collected into PAXgene Blood RNA tubes. Total RNA was extracted from the samples and reverse-transcribed into cDNA, and retina-specific markers were measured by quantitative real time PCR. In patients with ≧5 dips/hr, mRNA values for rhodopsin (P=0.05) and RPE65 (P=0.044) were significantly higher than in patients with <5 dips/hr. No change was seen in retinoschisin mRNA expression. In patients with preproliferative or proliferative DR, median levels for rhodopsin mRNA and RPE65 mRNA were 30% and 80% higher and retinoschisin mRNA was lower in patients with ≧5 dips/hr when compared to patients with <5 dips/hr. These results indicate that hypoxia may modulate expression of genes in the retina.

Introduction

Diabetic retinopathy (DR) is a common microvascular complication of diabetes and is an important cause of blindness in the developed world. Currently in the UK, a typical eye examination for a diabetic patient includes visual acuity assessment and digital retinal photography, and the degree of retinopathy is graded according to a scale for the number of abnormalities observed. Although this method is cost effective, it involves different specialist personnel, is very subjective, and requires experience and training for accurate assessment There is no objective and quantifiable method available as yet for the assessment of DR.

Rhodopsin is a visual pigment found exclusively in the rod cells of the retina which enables vision in low-light conditions (1). Rhodopsin mRNA is detectable in the circulation of healthy individuals and diabetic patients (2,3). Compared to findings in healthy subjects, rhodopsin mRNA was found to be significantly higher in diabetic subjects. It was observed that, apart from patients with proliferative DR, there was a tendency for rhodopsin mRNA levels to increase with increasing severity of retinopathy. Of interest, rhodopsin mRNA was found to be significantly higher in patients without retinopathy when compared to healthy controls. This led to the proposal that retinal damage may be present before the clinical signs develop in DR.

Hypoxia is defined as a lack of adequate oxygen supply. Obstructive sleep apnea (OSA) is associated with intermittent hypoxia, albeit intermittent and intrinsically linked with sympathetic nervous system activation. It has been proposed recently that hypoxia as seen in OSA is associated with DR (4). OSA is the most common form of sleep disordered breathing, characterized by cessation of airflow on account of complete or partial occlusion of the airway despite continuing respiratory effort. It is a common disorder which affects tip to 4% of adults and up to 2.5%/n of adults with type 2 diabetes mellitus. Studies have shown that OSA was more prevalent in patients with ocular disorders such as normal tension glaucoma (5). Higher incidence of visual field defects and optic nerve changes were reported in OSA when compared to age-matched controls (6). These findings led to the suggestion that examination of the eye may allow the identification of patients suffering from undiagnosed OSA (7).

Recently, it has been suggested that OSA is associated with DR. In a small study, 22 obese diabetic subjects with OSA were compared with 22 similarly obese diabetic subjects without OSA. Patients with OSA tended to suffer from a more aggressive form of DR, one characterized by multiple nerve fiber layer infarctions and diffuse maculate edema. It was suggested that hypertension and recurrent intermittent hypoxia seen in OSA may cause repetitive insults to the retina, thus aggravating DR (8).

Because rhodopsin mRNA has been associated with DR, and there is a possibility that DR may be associated with hypoxia, we were interested to see how hypoxia affects some retina specific mRNAs, including rhodopsin, RPE65, and retinoschisin.

The retinal pigment epithelium, RPE, is a single layer of pigmented cells forming a part of the blood/retina barrier. The RPE has many functions, including transportation of nutrients from the blood to the photoreceptors, phagocytosis of shed photoreceptor outer segments, and secretion of growth factors (9). RPE65 is a protein which is found and expressed exclusively in the RPE. In humans, mutations of RPE65 lead to a condition known as Leber's congenital amaurosis, or early-onset retinal dystrophy, a severe form of retinitis pigmentosa. The exact function of RPE65 is unknown, but knockout mice models have shown that in RPE65−/− mice, there was an over accumulation of all-trans-retinal in the RPE and 11-cis-retinal was found to be absent (10). More recent studies revealed that RPE65 plays a role in the recycling of 11-cis-retinal, a process known as the visual retinoid cycle. After initiation of vision, all-trans-retinal would need to be recycled into 11-cis-retinal, with isomerohydrolase being the enzyme responsible for the isomerization and hydrolysis of all-trans-retinal to 11-cisretinal. It has been suggested that RPE65 is a retinyl ester binding protein which acts as an insoluble substrate to the isomerohydrolase (11). It has also been demonstrated that RPE65 had the enzymatic activity to efficiently generate 11-cis-retinol from the all-trans-retinyl ester, leading to the proposal that RPE65 is the enzyme responsible for the isomerohydrolase activity (12).

Retinoschisin is a protein which is also found exclusively in the retinal tissue. It is encoded by the gene RS1 associated with the condition, X-linked juvenile retinoschisin, a recessively inherited condition characterized by maculate degeneration, which affects males in early life. Studies on the mouse retina have shown that retinoschisin is synthesized and secreted primarily by the photoreceptors in the retina (13,14). The exact function of this protein is unknown. Seventy percent of retinoscbisin has been shown to be made up of the discoidin domain, which functions in cell-cell adhesion; therefore, retinoschisin is generally regarded as a cell adhesion protein that plays a crucial role in maintaining the structural integrity of the retina (15). It has also been suggested that after synthesis and secretion, retinoschisin would reach the surface of the retinal cells and mediate interactions between photoreceptor, bipolar and Müller cells, contributing to the maintenance of the cytoarchitectural integrity of the retina (16). The aim of the study was to investigate the effect of intermittent hypoxia on circulating retina-specific mRNA for rhodopsin, RPE65, and retinoschisin, in type 2 diabetic patients.

Material and Methods

Type 2 diabetic patients attending Guy's and St Thomas' Hospital were recruited for the study, which was approved by the Local Research Ethics Committee. Patients with type 2 diabetes of at least 5 years' duration, with BMI>25 kg/m² and with digital retinal photography within 6 months of recruitment, were included in the study group.

After written consent was obtained from the subjects, the following measurements were made blood pressure; weight; height; and neck, waist, and hip circumference. Patients were shown how to use a PULSOX®-300i oxygen saturation monitor and were asked to wear it during sleep that night.

The following day, patients filled in a questionnaire about the quality of sleep the previous night and the data from the oximeter was downloaded onto a PC for analysis using a software called Download2001 (Stowood Scientific). Blood samples were then taken into two PAXgene™ Blood RNA tubes (Qiagen).

Whole blood RNA was extracted using PAXgene Blood RNA Kit strictly following the manufacturer's instructions. Whole blood RNA was then quantified using a spectrophotometer (Pharmacia GeneQuant RNA/DNA Calculator).

Extracted RNA was stored at −80° C. until required from cDNA synthesis. Reverse transcription was carried out using Superscript II reverse transcriptase following the manufacturer's instruction (Invitrogen Life Sciences). The cDNA generated was stored at −80° C. until quantitative real-time PCR.

Quantitative real-time PCR was carried out on 96-well optical reaction plates. These were prepared in a PCR dedicated fume cupboard Each plate was used to quantify rhodopsin, RPE65 or retinoschisin, and β-actin mRNA concentrations. β-actin cDNA was used to confirm amplification and act as an internal control. Each plate contained a 6-point standard curve, 16 samples, non-template control, and sterile water. The 6-point standard curves were from serial dilutions of DNA obtained from healthy human retina. 10 μL of cDNA was added into the wells along with 40 μL of PCR master mix. The PCR master mix was composed of primers and probes of the target of interest, TaqMan Universal PCR Master Mix, and sterile water. All samples were run in duplicate.

The plate was sealed with an optical adhesive cover and briefly centrifuged for 6 seconds using Allegra21R™ centrifuge to mix the samples and PCR master mix together. Finally, it was placed into the ABI Prism 7000 Sequence Detection System for quantitative realtime PCR, which included an initial phase of 2 minutes at 50° C., followed by 10 minutes at 95° C., and then up to 50 cycles of 15 seconds at 95° C. and 1 minute at 60° C. Results for rhodopsin mRNA were expressed as the ratio to total blood β-actin mRNA and total RNA. Statistical analysis was performed with SPSS (version 14.0). Mann-Whitney U test for non-parametric data was used to analyze the results. Patient characteristics were analyzed by one-way ANOVA where appropriate. Significance was defined as P<0.05.

Results

In total, 35 patients underwent overnight oximetry. The detection rate for rhodopsin mRNA and β-actin mRNA was 100%. The detection rates for RPE65 and retinoschisin were 99% and 91%, respectively.

In order to assess the precision of RNA extraction, 12 samples of blood were collected from a healthy individual into PAXGene Blood RNA tubes. These samples were extracted according to the RNA extraction protocol, and the quantity of total RNA was determined using spectrophotometric analysis. The mean concentration of extracted RNA was 6.17±0.41 μg/mL and the coefficient of variation (CV) was 6.7%.

To assess the analytical precision of the entire protocol, blood samples (n=12) were collected from a healthy individual; RNA was extracted from these samples and they were then reverse transcribed to cDNA and the markers quantified by real-time PCR. For each marker, critical threshold (Ct) values were used to calculate the intra-assay and inter-assay coefficient of variations. Intra-assay coefficient of variation (CV) varied from 0.7 to 3.8% and inter-assay CV varied from 3.7 to 4.3% (Table 2).

TABLE 2

Intra- and Inter-assay CVs for Each Retinal Specific Marker

| Retina-specific marker | Intra-assay CV (%) | Inter-assay CV (%) |
|---|---|---|
| Rhodopsin | 0.7 | 3.7 |
| RPE65 | 3.8 | 4.7 |
| Retinoschisin | 2.8 | 4.3 |

The number of times oxygen saturation decreased by 4% or greater from baseline saturation per hour and the percentage of sleep time spent with oxygen saturation<90% were the two parameters from the overnight oximetry used to examine the effects of oxygen desaturation on circulating retina-specific mRNA in diabetic patients.

Patients were divided into those with less than five 4% dips per hour (<5 dips/hr) and those with greater or equal to five 4% dips per hour (≧5 dips/hr). There was no significant difference in any characteristic between the two groups (Table 3).

TABLE 3

Characteristics of Patients with <5 dips/hr and those with ≧5 dips/hr according to the Number of Times Oxygen Saturation Decreased by 4% or More per Hour$^a$

|  | Patients with <5 dips/hr | Patients with ≧5 dips/hr |
|---|---|---|
| N | 22 | 13 |
| Age (years) | 59 ± 12.0 | 61 ± 6.4 |
| Gender (M/F) | 14/8 | 10/3 |
| Duration of diabetes (years) | 16 ± 8.3 | 17 ± 8.0 |
| BMI (kg/m2) | 30.6 ± 7.3 | 30.0 ± 4.5 |
| Systolic BP (mmHg) | 142.4 ± 14.1 | 149.2 ± 19.2 |
| Diastolic BP (mmHg) | 78.4 ± 11.2 | 82.6 ± 10.3 |
| Neck circumference (cm) | 38.1 ± 3.5 | 39.2 ± 3.7 |
| Waist:hip ratio | 1.0 ± 0.1 | 1.0 ± 0.1 |
| ESS | 7.59 ± 3.6 | 7.6 ± 3.7 |
| HbA1c (%) | 8.1 ± 1.6 | 8.5 ± 1.4 |
| ACR | 3.49 ± 3.6 | 4.07 ± 6.3 |
| Plasma creatinine (μmol/L) | 89.2 ± 22.3 | 104.2 ± 57.8 |
| Hb (g/dL) | 13.0 ± 1.7 | 13.6 ± 1.3 |
| Cholesterol (mmol/L) | 4.3 ± 0.8 | 4.1 ± 0.9 |
| Visual acuity | 6/8.8 ± 3.5 | 6/10.2 ± 3.4 |

$\alpha$Results are given as mean and SD. BMI, body mass index, ESS, Epworth sleepiness scale; HbA1c, glycosylated hemoglobin; ACR, albumin-creatinine ratio; Hb, hemoglobin.

Figure 4:
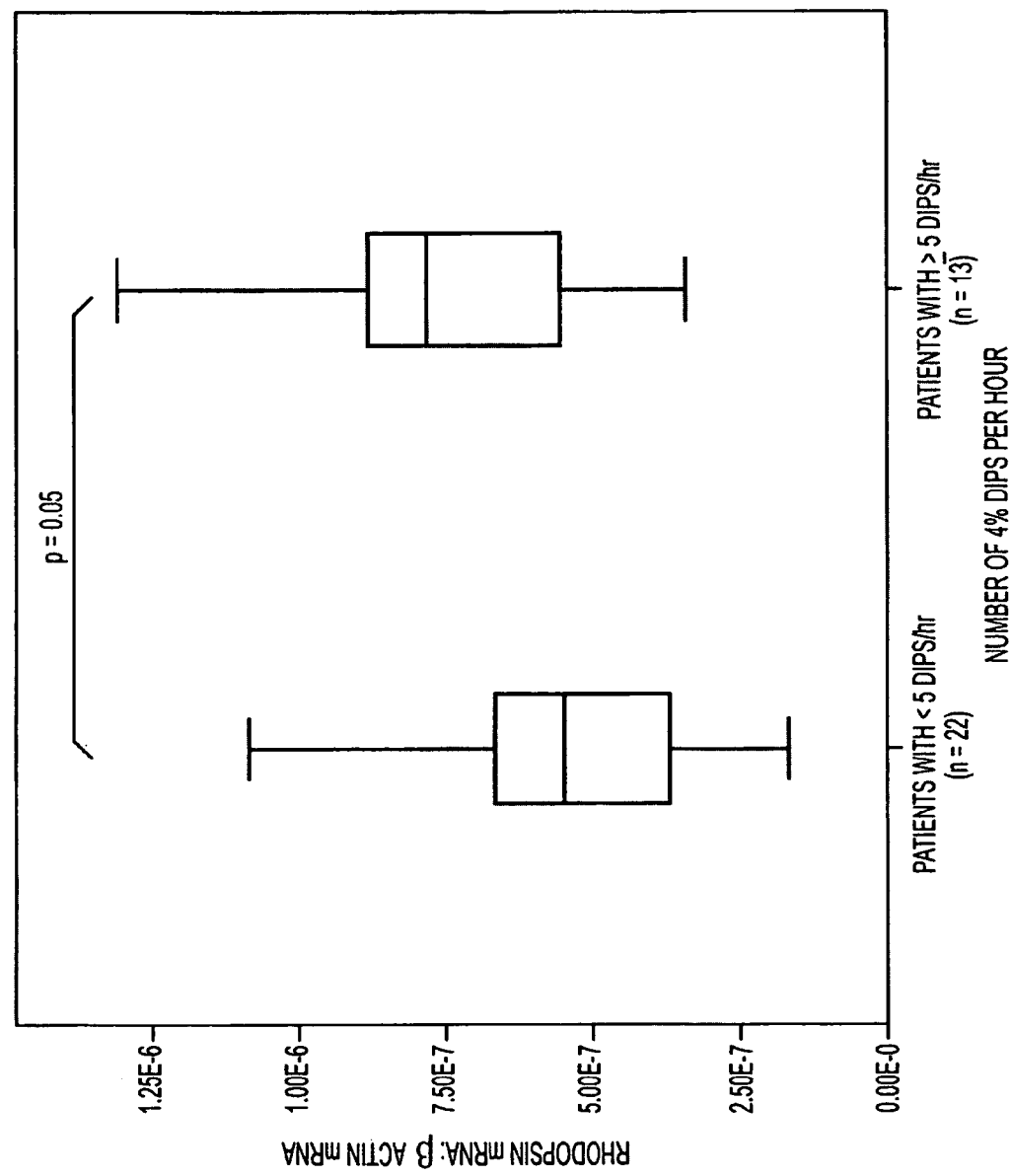
FIG. 4. Circulating rhodopsin mRNA levels in patients with <5 dips/hr and patients with ≧5 dips/hr. The box plot displays median (thick solid line), interquartile range (shaded box), and range (whiskers).
Figure 5:
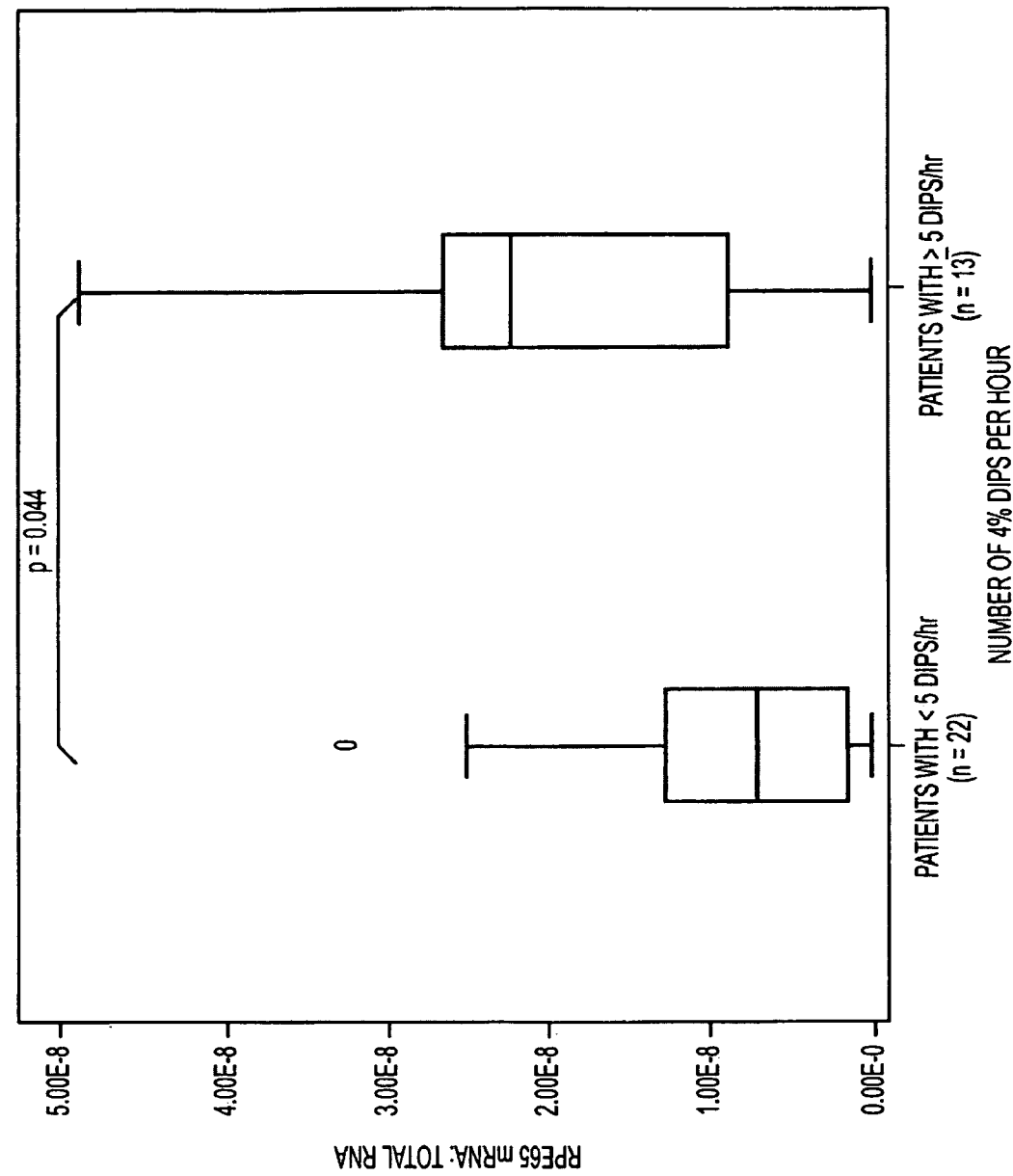
FIG. 5. Circulating RPE65 mRNA levels in patients with <5 dips/hr and patients with ≧5 dips/hr when normalized against total RNA. ○ denotes outliers. The box plot displays median (thick solid line), interquartile range (shaded box), and range (whiskers).

Rhodopsin mRNA levels in patients with ≧5 dips/hr when compared with patients with <5 dips/hr were significantly higher (P=0.05) (FIG. 4). Patients with ≧5 dips/hr also had significantly higher RPE65 mRNA levels when compared to patients with <5 dips/hr (P=0.044) (FIG. 5). There was no significant difference in retinoschisin mRNA levels between the two groups.

The percentage of sleep time with oxygen saturation (SpO$_2$)<90% was used as another measure of hypoxia. Patients were divided into those who spent less than 2% of their sleep time with SpO$_2$<90% (<2%) and those who spent more than 8% of their sleep time with SpO$_2$<90% (>8%). There was no difference in any characteristics between the two groups. Rhodopsin, RPE65, and retinoschisin mRNA levels were not different between patients who spent <2% of their sleep time with SpO$_2$<90% and those who spent >8% of their sleep time with SpO$_2$<90%.

Figure 6:
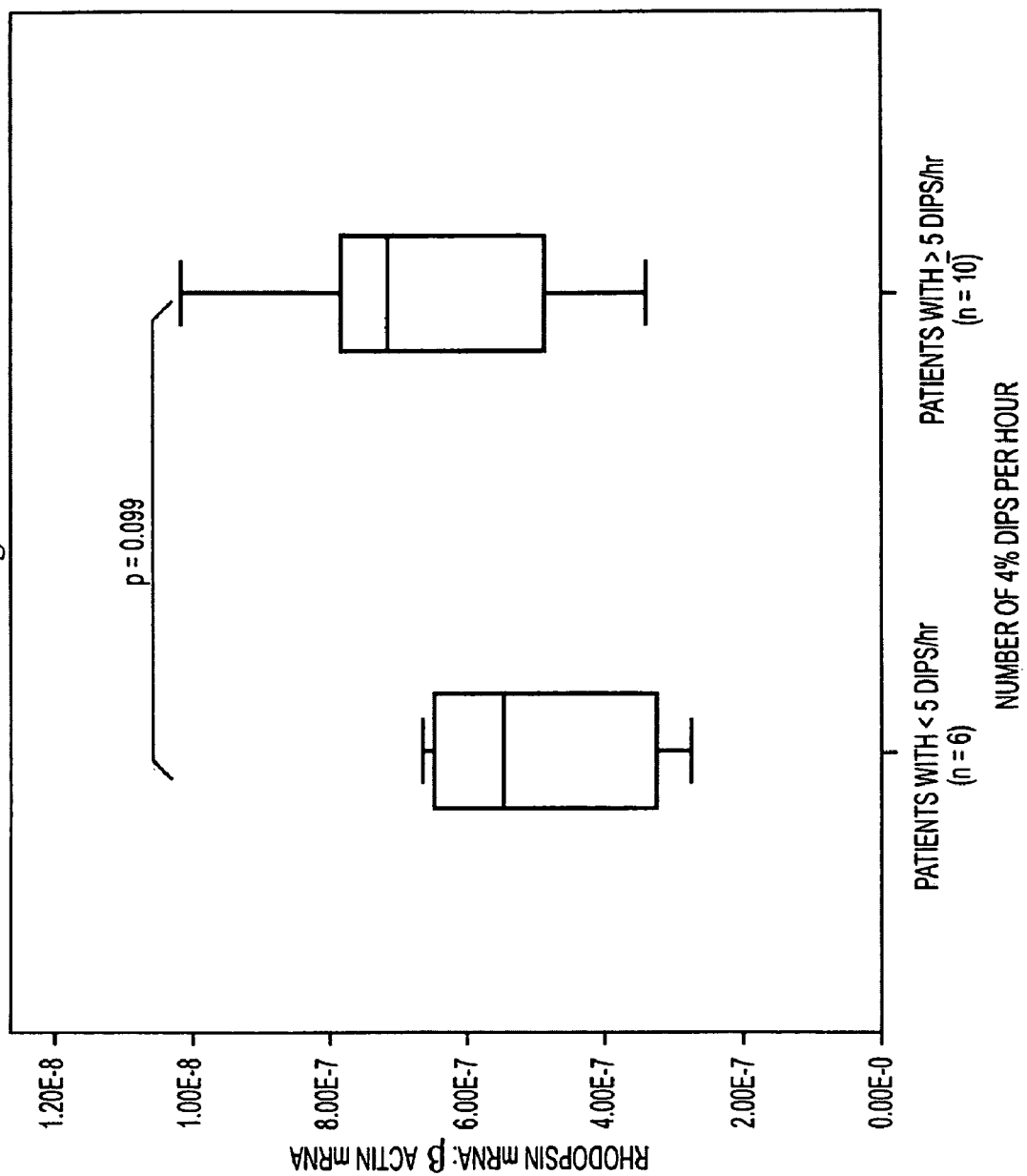
FIG. 6. Circulating rhodopsin mRNA levels in patients with preproliferative or proliferative DR and <5 dips/hr and patients with preproliferative or proliferative DR and ≧5 dips/hr. The box plot displays median (thick solid line), interquartile range (shaded box), and range (whiskers).
Figure 7:
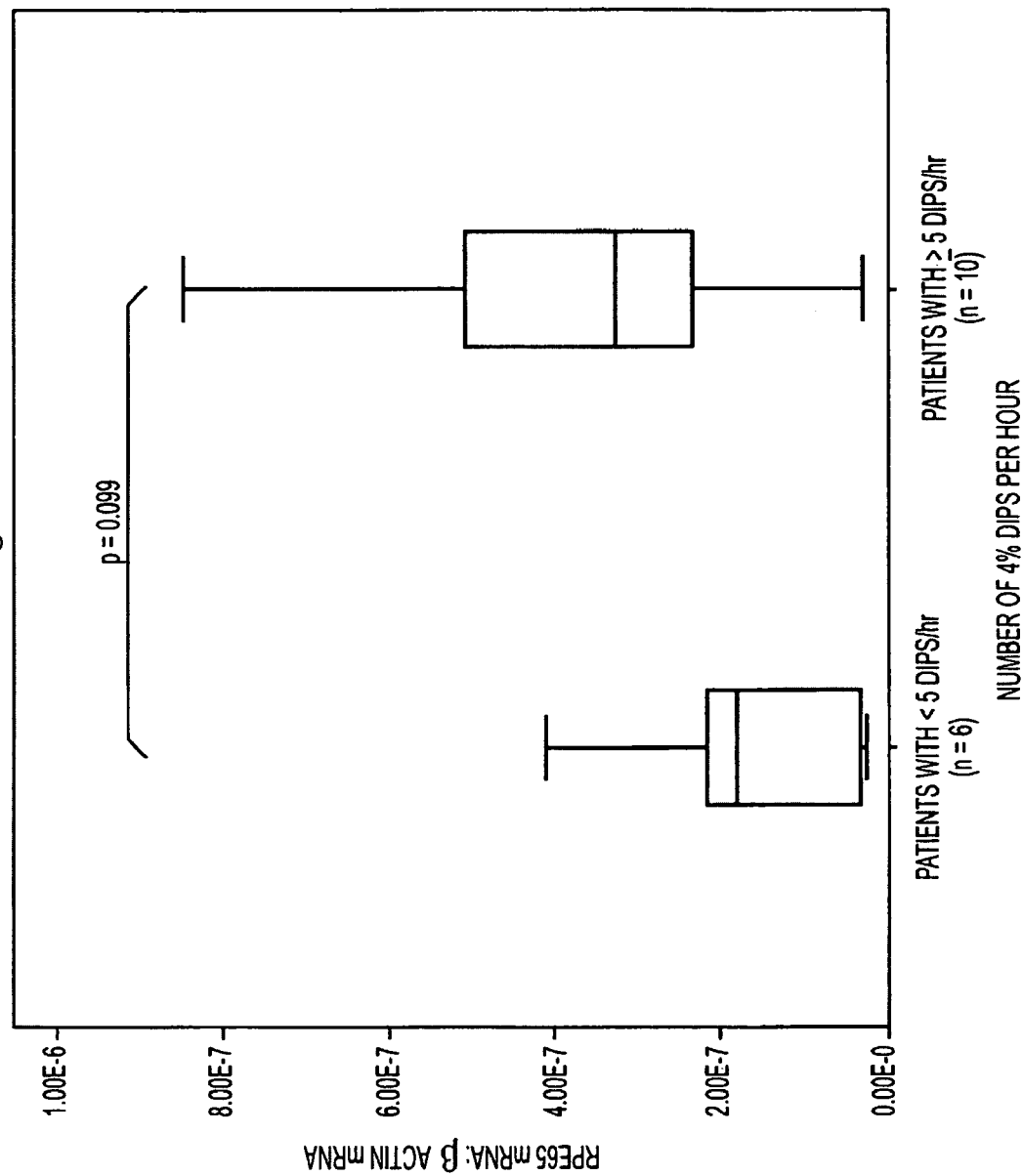
FIG. 7. Circulating RPE65 mRNA levels in patients with preproliferative or proliferative DR and <5 dips/hr and patients with preproliferative or proliferative DR and ≧5 dips/hr. The box plot displays median (thick solid line), interquartile range (shaded box), and range (whiskers).
Figure 8:
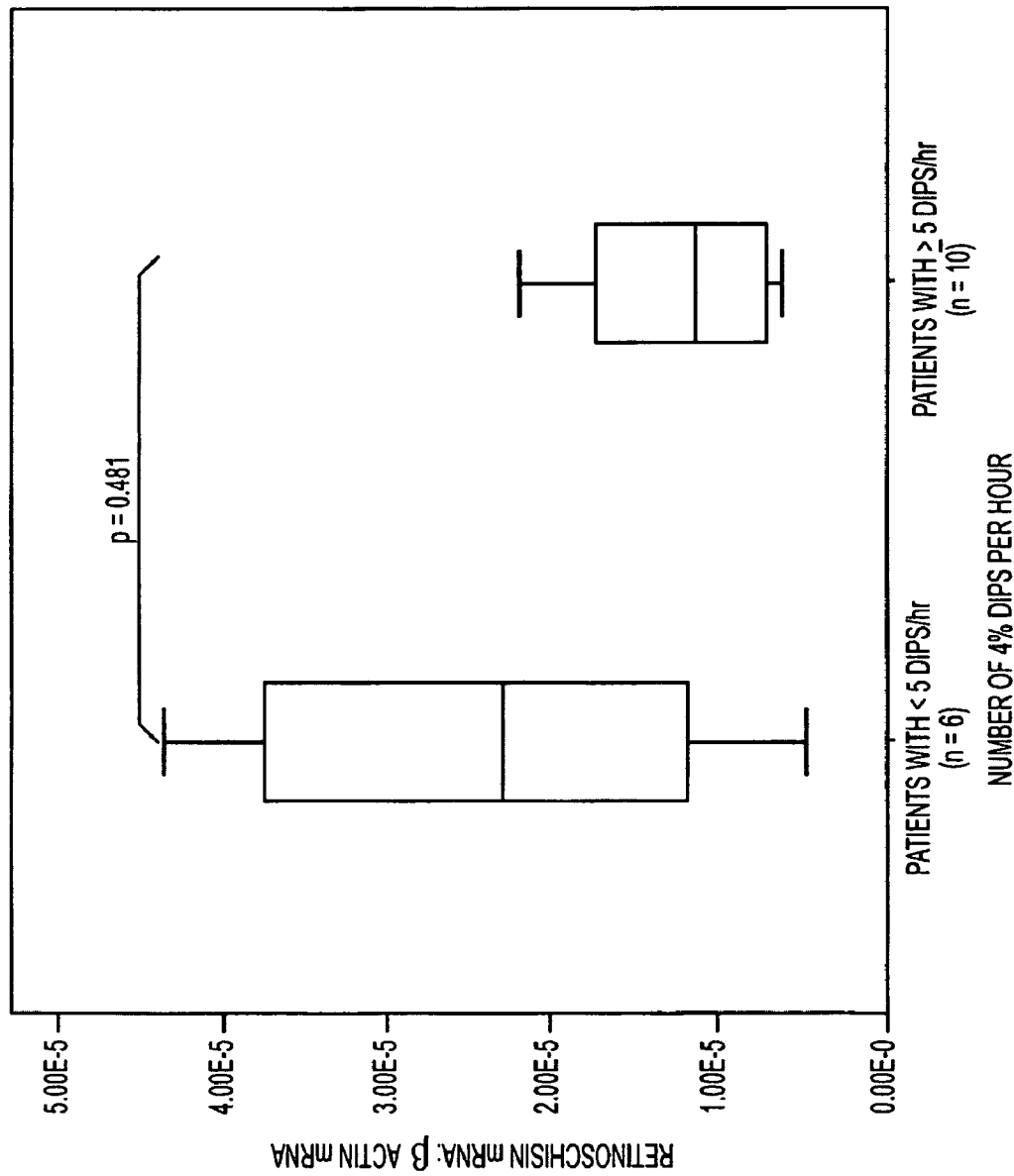
FIG. 8. Circulating retinoschisin mRNA levels in patients with preproliferative or proliferative DR and <5 dips/hr and patients with preproliferative or proliferative DR≧5 dips/hr. The box plot displays median (thick solid line), interquartile range (shaded box), and range (whiskers).

There were 16 patients with preproliferative or proliferative DR and they were divided into those whose oxygen saturation decreased by 4% less than five times per hour, (<5 dips/hr) (n=6) and those with more or equal to five times per hour (≧5 dips/hr) (n=10). There was no difference in any characteristics between the two groups. Median rhodopsin mRNA level was 30% higher (FIG. 6), RPE65 mRNA level was 80% higher (FIG. 7), and retinoschisin mRNA level was 50% lower in patients with ≧5 dips/hr compared to those with <5 dips/hr (FIG. 8). However, these differences were not statistically significant.

Discussion

Nucleic acids (DNA and RNA) are present in the circulation and circulating retina-specific rhodopsin mRNA has been associated with diabetic retinopathy (DR). Hypoxia as seen in obstructive sleep apnea (OSA), the most common form of sleep-disordered breathing, has been suggested to be associated with DR. The primary aim of this study was to investigate the effect of hypoxia on circulating retina-specific mRNA.

The coefficients of variations (CVs) for the inter- and intra-assays of all retina-specific mRNA markers were satisfactory and showed that the protocol was highly reproducible. Detection rates of these markers ranged from 91% and 98% for retinoschisin and RPE65 mRNA, respectively, to 100% for both rhodopsin and γ-actin mRNA. There is now abundant evidence for the existence of mRNA in the circulation; for example, thyroglobulin (Tg) mRNA has been detected in patients with thyroid cancer and telomerase reverse transcriptase protein (hTERT) mRNA was detected in patients with breast cancer and hepatocellular carcinoma (HCC) (17-19). It has been proposed that RNA may be present in the circulation complexed to lipids or contained in apoptotic bodies, protecting it from degradation by nucleases (20,21).

Because of the small number of the cohort, patients were divided into two groups according to their number of 4% dips per hour and a cut-off point of 5 was used. No universally agreed-upon cut-off point is used to define OSA from the number of episodes of oxygen desaturation. However, cut-off points of 5, 10, or 15 dips per hour have been used (22). No clinical characteristics were found to be different between the two groups of patients.

Levels of rhodopsin mRNA and RPE65 mRNA were found to be higher in patients with ≧5 dips/hr compared to patients with <5 dips/hr. There was no difference in retinoschisin mRNA levels between the two groups of patients. These findings suggest that higher levels of rhodopsin and RPE65 mRNA were associated with hypoxia.

Another parameter used to measure oxygen desaturation was percentage of sleep time with SpO$^2$<90%. Patients were divided into two groups using two arbitrary cut-off points: less 2% or greater than 8%. These cut-off points were used in an attempt to identify patients with the most severe hypoxia and those with the least severe hypoxia, respectively. There was no difference in any retina-specific mRNA levels between these two subgroups. These results contrast with the previous findings using the number of 4% dips per hour, which showed that hypoxia was associated with higher levels of circulating rhodopsin and RPE65 mRNA. This may be ascribed to the smaller number of patients studied using the parameter of percentage of sleep time with SpO$_2$<90%.

Since it had been shown previously that DR is associated with rhodopsin mRNA levels, it can be argued that the difference seen in rhodopsin and RPE65 levels between patients with ≧5 dips/hr and patients with <5 dips/hr was due to different stages of DR in those patients. To overcome this potential confounding factor, patients with either preproliferative or proliferative DR were examined. Median levels of rhodopsin mRNA and RPE65 mRNA were found to be higher by 30% and 80%, respectively, in patients with ≧5 dips/hr compared with those with <5 dips/hr. Median levels of retinoschisin mRNA were lower in patients with ≧5 dips/hr when compared to those with <5 dips/hr. These results showed that even after taking DR into account, oxygen desaturations were still associated with higher levels of rhodopsin mRNA and RPE65 mRNA and lower levels of retinoschisin mRNA.

The mechanisms by which hypoxia modulates circulating retina-specific mRNA levels are unknown. The retina is a highly metabolically active tissue which requires a continuous supply of oxygen (23). The rod cells of the retina are involved in dark adaptation responses, which are highly ATP-dependent, thus consuming a significant amount of retinal oxygen supply. Studies on rod photoreceptor knockout mice (Rho−/−) showed that photoreceptor loss reduced retinal oxygen usage and subsequent development of hypoxia-related gene expression (24). Furthermore, other animal studies have revealed that hypoxia precipitated the death of rod cells, and that hyperoxia was associated with increased rod cell survival (25,26). The findings of these studies suggest that hypoxia can cause rod cell deaths. It has also been shown previously that circulating mRNA levels were elevated in circumstances involving cell death. Therefore, it is possible that in hypoxia, increased levels of rhodopsin mRNA were released into the circulation as a direct result of the death of rod cells. Very few studies have investigated the effect of hypoxia on the retinal pigment epithelium. A study on cultured RPE showed that RPE cells were unlikely to suffer from hypoxic injury (27). However, RPEF65 is known to be involved in the process of recycling trans-retinal to cis-retinal, which may require a high oxygen supply. Hypoxia has been proposed to cause retinal neuronal damage via nitric oxide (NO) and its interactions with free radicals (28). This can be extended further to suggest that hypoxia may also cause damage or death of RPE cells via pathways involving NO and, as a result of this insult, increased levels of RPE65 mRNA are released into the circulation.

Hypoxia is also known to modulate expression of many genes, including those involved in erythropoiesis, angiogenesis, and lipid metabolism (29-32). Furthermore, it is widely acknowledged that hypoxia-inducible factor 1 (HIF-1) plays a critical role in the modulation of gene expression induced by hypoxia (33). HIF-1 is able to activate more than 70 genes at the transcriptional level, and it has been suggested that this is probably an underestimation by an order of magnitude (34). HIF-1 is known to be involved in both up- and downregulation of gene expressions. One of the genes known to be upregulated by HIF-1 is vascular endothelial growth factor (VEGF), a growth factor that increases capillary permeability and stimulates angiogenesis in proliferative DR. Since HIF-1 is involved in the modulation of gene expressions induced by hypoxia in so many tissues, the possibility exists that hypoxia may upregulate the expression of rhodopsin mRNA and RPE65 mRNA and downregulate the expression of retinoschisin mRNA via HIF-1.

Conclusions

Intermittent hypoxia was associated with higher levels of circulating rhopdopsin mRNA and RPE65 mRNA and a lower level of circulating mRNA for retinoschisin. These associations were still present even after taking the degree of diabetic retinopathy into account. Hypoxia may affect the expression of different genes via different mechanisms.

REFERENCES

1. Hargrave, P. A. 2001. Rhodopsin structure, function, and topography: the Friedenwald lecture. *Invest. Ophthalmol. Vis. Sci,* 42: 3-9.
2. Hamaoui, K. et al. 2004. Concentration of circulating rhodopsin mRNA in diabetic retinopathy. *Clin. Chem.* 50: 2152-2155.
3. Butt, A. N. et al. 2006. Circulating nucleic acids and diabetic complications. *Ann. N.Y. Acad. Sci.* 1075: 258-270.
4. Sinclair, S. et al. 2005. Diabetic retinopathy: treating systemic conditions aggressively can save sight. *Cleveland Clin. J. Med.* 72: 447-454.
5. Marcus, D. M. et al. 2001. Sleep disorders: a risk factor for normal-tension glaucoma? *J. Glaucoma* 10: 177-183.
6. Tsang, C. S. L. et al. 2006. Moderate to severe obstructive sleep apnoea in patients is associated with a higher incidence of visual field defect. *Eye* 20: 38.
7. Abdal, H. et al. 2006. The eye in sleep apnea syndrome. *Sleep Med.* 7: 107-115.
8. Sinclair, S. H. et al. 2007. A putative relation between obstructive sleep apnea and diabetic maculate edema associated with nerve fiber layer infarcts. *Arch. Ophthalmol.*
9. Strauss, O. 2005. The retinal pigment epithelium in visual function. *Physiol. Rev.* 85; 845-881.
10. Redmond, M. et al. 1998. RPE65 is necessary for production of 11-cis-vitamin A in the retinal visual cycle. *Nat. Genet.* 20: 344-351.
11. Mata, N. L. et al. 2004. Rpe65 is a retinyl ester binding protein that presents insoluble substrate to the isomerase in retinal pigment epithelial cells. *J. Biol. Chem.* 279: 635-643.
12. Moiseyev, G. et al. 2005. RPE65 is the isomerohydrolase in the retinoid visual cycle. *PNAS* 102: 12413-12418.
13. Reid, S. N. M. et al. 1999. The mouse X-linked juvenile retinoschisis cDNA expression in photoreceptors. *Gene* 227: 257-266.
14. Molday, R. S. 2007. Focus or molecules: retinoschisin (RS1). *Exp. Eye Res.* 84: 227-228.
15. Molday, L. L. et al. 2001. Expression of X-linked retinoschisis protein RS1 in photoreceptor and bipolar cells. *Invest. Ophthalmol. Vis. Sci.* 42: 816-825.
16. Reid, S. N. et al. 2003 Retinoschisin, a photoreceptor secreted protein, and its interaction with bipolar and muller cells. *J. Neurosci.* 23: 6030-6040.
17. Li, D. et al. 2004. Real-time quantitative PCR measurement of thyroglobulin mRNA in peripheral blood of thyroid cancer patients and healthy subjects. *Ann. N. Y. Acad. Sci.* 1022: 147-151.
18. Chen, X. Q. et al. 2000. Telomerase RNA as a detection marker in the serum of breast cancer patients. *Clin. Cancer Res.* 6: 3823-3826.
19. Miuraa et al. 2003. Sensitive detection of human telomerase reverse transcriptase mRNA in the serum of patients with hepatocellular carcinoma. *Oncology* 64: 430-434.
20. Halicka, H. D. et al. 2000 Segregation of RNA and separate packaging of DNA and RNA in apoptotic bodies during apoptosis. *Exp. Cell Res.* 260: 248-256.
21. Rosi, A. et al. 1988. RNA-lipid complexes released from the plasma membrane of human colon carcinoma cells. *Cancer Lett.* 39: 1588.
22. Netzer, N. et al. 2001. Overnight pulse oximetry for sleep-disordered breathing in adults: a review. *Chest* 120: 625 633.

23. Wangsa-Wirawan, N. D. & R. A. Linsenmeier. 2003. Retinal oxygen: fundamental and clinical aspects. *Arch. Opthalmo.* 121: 547-557.
24. De Gooyer, T. E. et al. 2006. Rod photoreceptor loss in rho −/− mice reduces retinal hypoxia and hypoxia regulated gene expression. *Invest. Ophthalmol Vis. Sci.* 47: 5553-5560.
25. Maslim, J. et al. 1997. Tissue oxygen during a critical developmental period controls the death and survival of photoreceptors. *Invest. Ophthalmol. Vis. Sci.* 38: 1667-1677.
26. Valter, K. et al. 1998. Photoreceptor dystrophy in the RCS rat: roles of oxygen, debris, and bFGF. *Invest. Ophthalmol. Vis. Sci.* 39: 2427-2442.
27. Nash, R. W. et al. 1994. The response of cultured human retinal pigment epithelium to hypoxia: a comparison to other cell types. *Invest. Opthalmol. Vis. Sci.* 35:2850-2856.
28. Kaur, C. et al. 2006. Early response of neurons and glial cells to hypoxia in the retina. *Invest. Ophthalmol. Vis. Sci.* 47:1126-1141.
29. Fandrey, J. 2004. Oxygen-dependent and tissue specific regulation of erytbropoietin gene expression. *Am. J. Physiol. Regul. Integr. Comp. Physiol.* 286: R977-988.
30. Li, J. et al. 2005. Chronic intermittent hypoxia upregulates genes of lipid biosynthesis in obese mice. *J. Appl. Physiol.* 99: 1643-1648.
31. McColm, J. R. et al. 2004. VEGF isoforms and their expression after a single episode of hypoxia or repeated fluctuations between hyperoxia and hypoxia: relevance to clinical ROP. *Mol. Vis.* 10: 512-520.
32. Stockmann, C. & J. Fandrey. 2006. Hypoxia-induced erythropoietin production: a paradigm for oxygen regulated gene expression. *Clin. Exp. Pharmacol. Physiol* 33: 968-979.
33. Greijer, A. E. et al. 2005. Up-regulation of gene expression by hypoxia is mediated predominantly by hypoxia-inducible factor 1 (HIF-1). *J. Pathol.* 206: 291.
34. Semenza, G. L. 2004. Hydroxylation of HIF-1: Oxygen sensing at thermolecular level. *Physiology* 19: 176-182.

Example 4

Hypertension and Circulating mRNA for 11β-Hydroxysteroid Dehydrogenase Type II

Summary

Circulating DNA and mRNA for 11β-hydoxysteroid dehydrogenase (HSD) type II were measured in patients with hypertension and in healthy subjects. DNA and RNA levels in hypertensive patients and controls were quantified using real-time RT-PCR. Messenger RNA for 11β-HSD type II was significantly lower in the hypertensive patients (median: 0.18) (P=0.032) than in healthy subjects (median: 0.42). Plasma DNA was also significantly lower (P=0.016) in hypertension. Measurement of mRNA for 11β-HSD type II therefore provides a basis for a test for susceptibility to hypertension.

Introduction

Hypertension is a very common disease worldwide and is an important public health challenge. One of the main factors contributing to the development of hypertension is salt intake. It has been shown that increased salt intake is associated with increased blood pressure (1). However, not all subjects with high salt intake develop hypertension, suggesting that some subjects are more salt-sensitive than others. The mechanism of salt sensitivity is not fully understood, but has been shown to be common in people of black origin (1).

Figure 9:
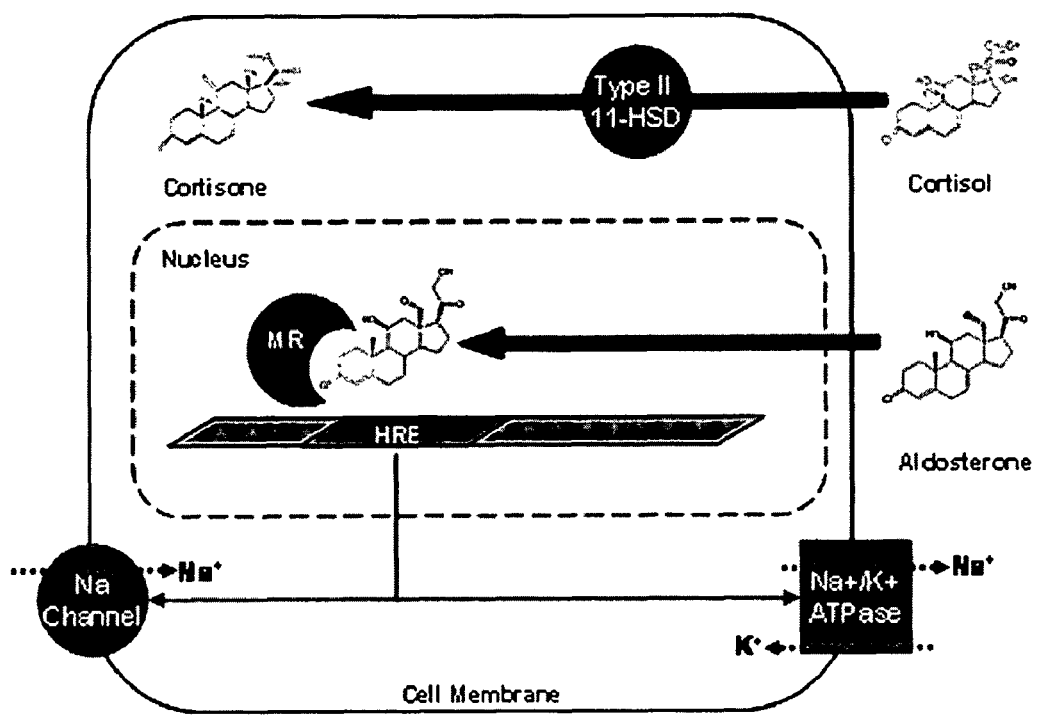
FIG. 9. Illustration of apparent mineralocorticoid excess (AME). Top: normal mineralocorticoid target cell can be seen in a renal cortical collecting duct. Aldosterone occupies nuclear receptors (MR) that bind to hormone-response elements, increasing transcription of genes and directly or indirectly increasing activities of apical sodium (Na) channels and the basolateral sodium-potassium (Na/K) ATPase. This increases resorption of sodium from and excretion of potassium into the tubular lumen. Cortisol, which circulates at higher levels than aldosterone, cannot occupy the receptor because it is oxidized to cortisone by 11-HSD type II. Bottom: cell from a patient with the AME syndrome. Because 11-HSD type II is absent, cortisol inappropriately occupies mineralocorticoid receptors, leading to increased gene transcription, increased activity of sodium channels and the Na/K ATPase, increased resorption of sodium, and excretion of potassium, and hypertension.
Figure 9:
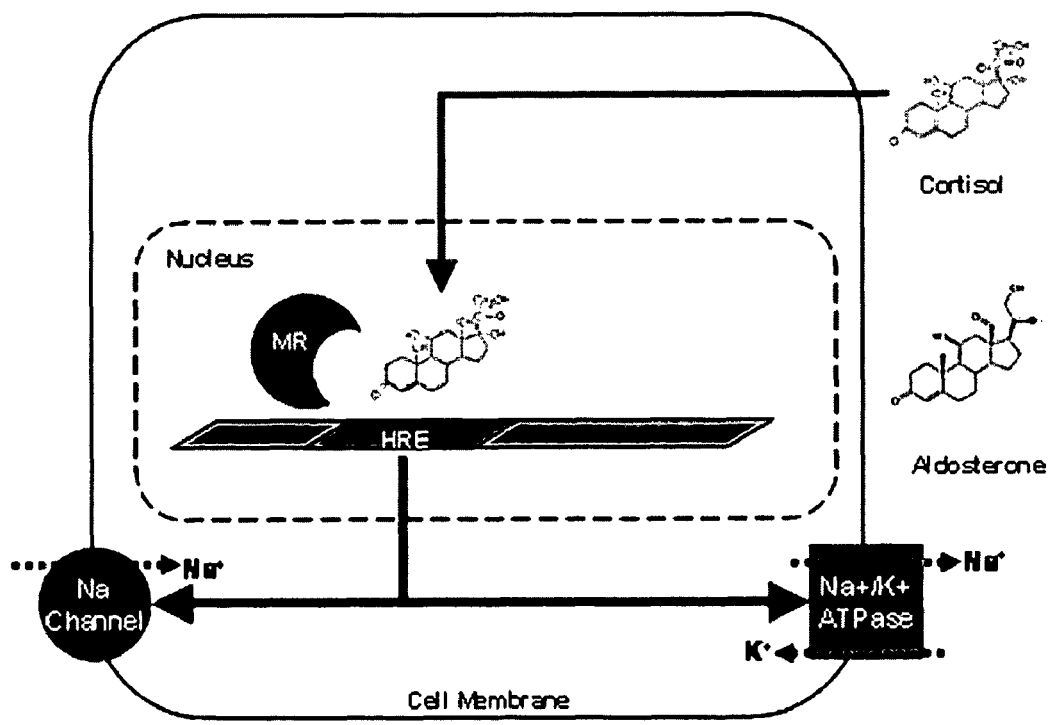

Hydroxysteroid dehydrogenase (HSD) enzymes are tissue-specific enzymes that convert prehormones into active hormones and vice versa. The 11β-hydroxysteroid dehydrogenase is involved in the metabolism of cortisol. There are two types of this enzyme. Type I 11β-HSD catalyzes the conversion of cortisone to cortisol using NADP(H) as cofactor, and it is expressed in a variety of tissues, including liver, lung, testis, colon, and kidney. Type II 11β-HSD converts cortisol (an active hormone) into cortisone (an inactive hormone) in the kidney, preventing glucocorticoids from binding to the type I mineralocorticoid receptor. Mutations of the gene encoding the type II enzyme causes apparent mineralocorticoid excess (AME), a form of salt-sensitive monogenic hypertension (FIG. 9). Thus it has been suggested that minor abnormalities of this enzyme may explain salt sensitivity in essential hypertension (2).

Recent studies have shown that measuring cell-free plasma DNA may have prognostic and diagnostic value. Plasma RNA and plasma DNA have been reported to be a useful prognostic markers in trauma (3) and critically ill patents (4) respectively. Tissue-specific circulating mRNA has been measured in thyroid cancer patients (5), and mRNA for circulating rhodopsin has been determined in patients with diabetic retinopathy (6). In this study, we have measured mRNA for 11β-HSD type IT and DNA in hypertensive patients and healthy subjects.

Materials and Methods

Samples were collected from healthy subjects and hypertensive patients into EDTA tubes (Becton Dickinson) and PAXgene™ Blood RNA Tubes (PreAnalytiX) which contain an additive that stabilizes RNA. The PAXgene RNA tubes, along with the cell-free plasma that had been separated from the EDTA tubes, were stored at −80° C. until required for further processing.

Ethics approval for this study granted by the local Research Ethics Committee. The patients were recruited from the hypertension clinics at St Thomas' and Guy's Hospitals, and informed consent was obtained form all subjects. Healthy subjects were not on any medication and there was no history of hypertension, Hypertensive patients were either newly diagnosed or were receiving antihypertensive medication.

DNA was extracted from cell-free plasma by using the Blood and Body Fluid Spin Protocol of the QIAamp DNA Blood Mini Kit. Whole blood RNA was extracted using the PAXgene Blood RNA Kit, including treatment with DNAse I to prevent genomic DNA contamination, strictly following the manufacturer's instruction (QIAgen). The QIAamp Viral RNA Mini Kit was used to extract RNA from cellfree plasma. Extracted RNA was stored at −80° C. until required for cDNA synthesis. Reverse transcription was carried out using Super-Script II™ reverse transcriptase following the manufacturer's instructions (Invitrogen Life Sciences, Scotland). The cDNA generated was stored at −80° C. until required for quantification, Separately, samples were also subjected to the above procedure, with the exception that SUPERSCRIPT II was replaced with water (negative control).

The ABI 7000 Sequence Detection System (PE Applied Biosystems) was used to amplify cDNA and quantitate mRNA for 11β-HSD type II and β-actin using sequence-specific oligonucleotide probes and intron-spanning specific primers. β-actin mRNA was measured as a reference marker. β-actin cDNA was amplified using the Pre-Developed Assay Reagents Taqman® assay (PE Applied Biosystems). In the case of the 11β-HSD type II, 900 nM forward and reverse primer, 250 nM probe, X2 Taqman_Universal Master Mix (25 μL) and cDNA sample (10 μL) were present in each reaction. For all assays, standards and samples were analyzed in duplicate in a final reaction volume of 50 μL. Standard curves were prepared from serial dilutions of cDNA (Clontech) obtained from normal healthy human kidney. A water blank was also incorporated in each run for the respective assays. These marker assays were ran simultaneously with β-actin on 96-well optical reaction plates. PCR amplification included an initial phase of 2 minutes at 50° C., followed by 10 minutes at 95° C., and then by 40 cycles of 15 seconds at 95° C. and 1 min at 60° C. Statistical analysis was performed using SPSS 10. Differences in the measured expression of mRNA between groups were analyzed by Mann-Whitney U-test. A P value of less than 0.05 was considered statistically significant.

Results

TABLE 4

Characteristics of Healthy Subjects and Hypertensive Patients

| | Healthy controls (N = 10) | Hypertensive patients (N = 23) |
|---|---|---|
| Age: mean (range) | 50 (35-60) | 52 (34-77) |
| Sex | 6M/4F | 13M/10F |
| BMI | — | 23-39.8 (31.2 ± 5.1) |
| Race | 5B/5C | 10B/13C |
| Systolic BP (mmHg) | — | 140-203 (187.6 ± 29.1) |
| Diastolic BP (mmHg) | — | 75-104 (89.4 ± 9.6) |
| Renin (pg/mL per hour) | — | caucasians = 1.06 ± 0.5; blacks = 0.8 ± 0.6 (reference range, 1.1-2.7)a |
| Aldosterone (reference range, 100-450)a | — | caucasians = 197 ± 96; blacks = 255 ± 150 |
| Ratio [aldosterone:renin ratio (PA/PRA)] | — | caucasians = 425 ± 377; blacks = 391 ± 225 |

N = number of subjects;
M = male;
F = female.
aRange after overnight recumbency.

Figure 10:
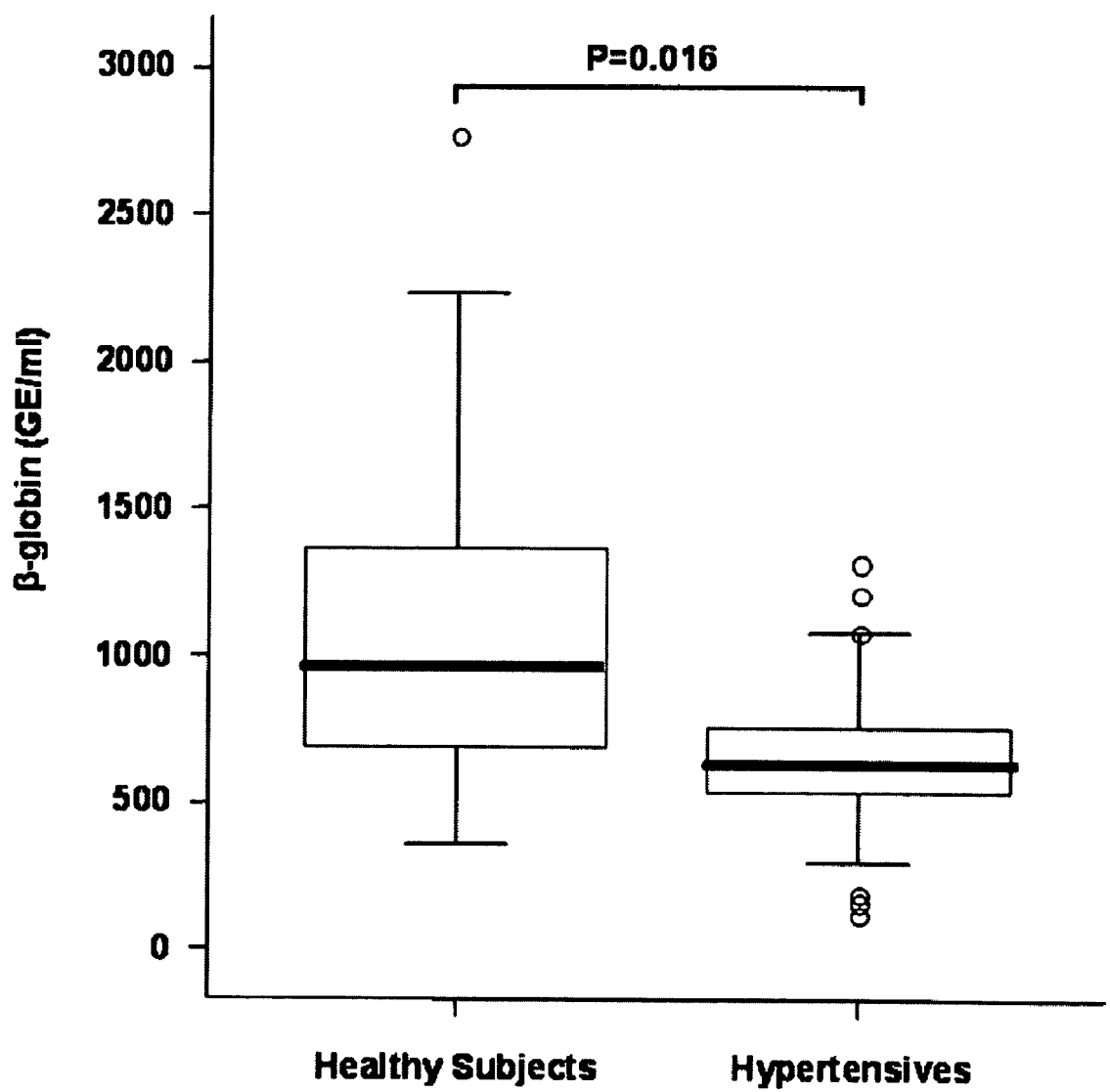
FIG. 10. Plasma DNA levels in healthy subjects and hypertensive subjects. The lines inside the boxes denote the medians; the boxes mark the interval between the 25th and 75th percentiles; and the whiskers denote the interval between the 10th and 90th percentiles.

Table 4 shows the characteristics of the two groups. Nearly 50% of the subjects were of black origin in both groups. The renin activity and aldosterone/renin ratio were lower in the black group than in the Caucasians, but the differences did not reach significance. FIG. 10 shows the plasma β-globin levels in the two groups. Plasma β-globin levels in the hypertensive group (median: 639 genome equivalents (GE)/mL, range: 355-2,765) was significantly lower compared to healthy controls (median: 964 GE/mL, range: 118-1,311) (P=0.016).

Figure 11:
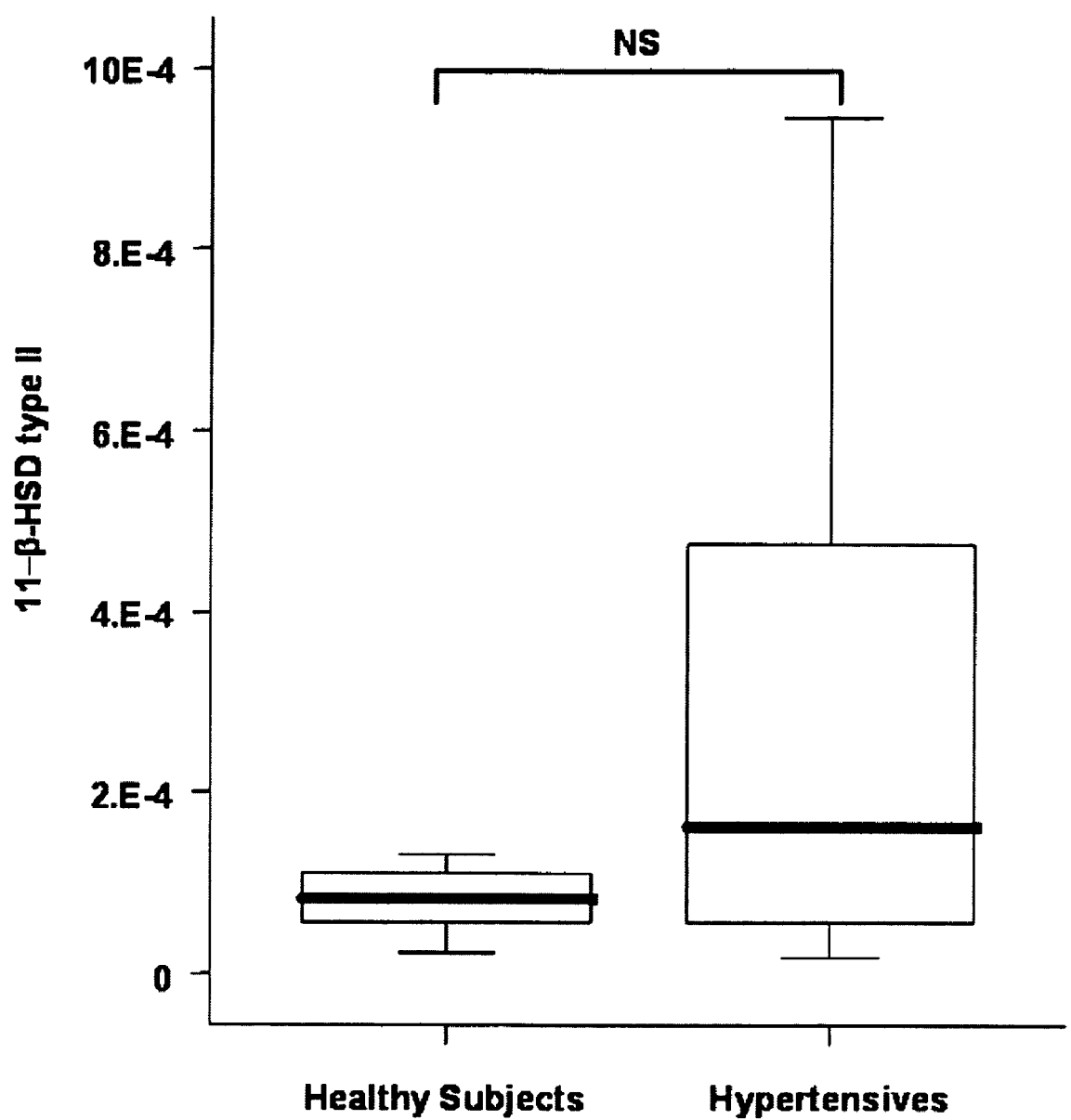
FIG. 11. Whole blood mRNA for 11β-HSD type II in healthy subjects and hypertensives, normalized against β-actin.
Figure 12:
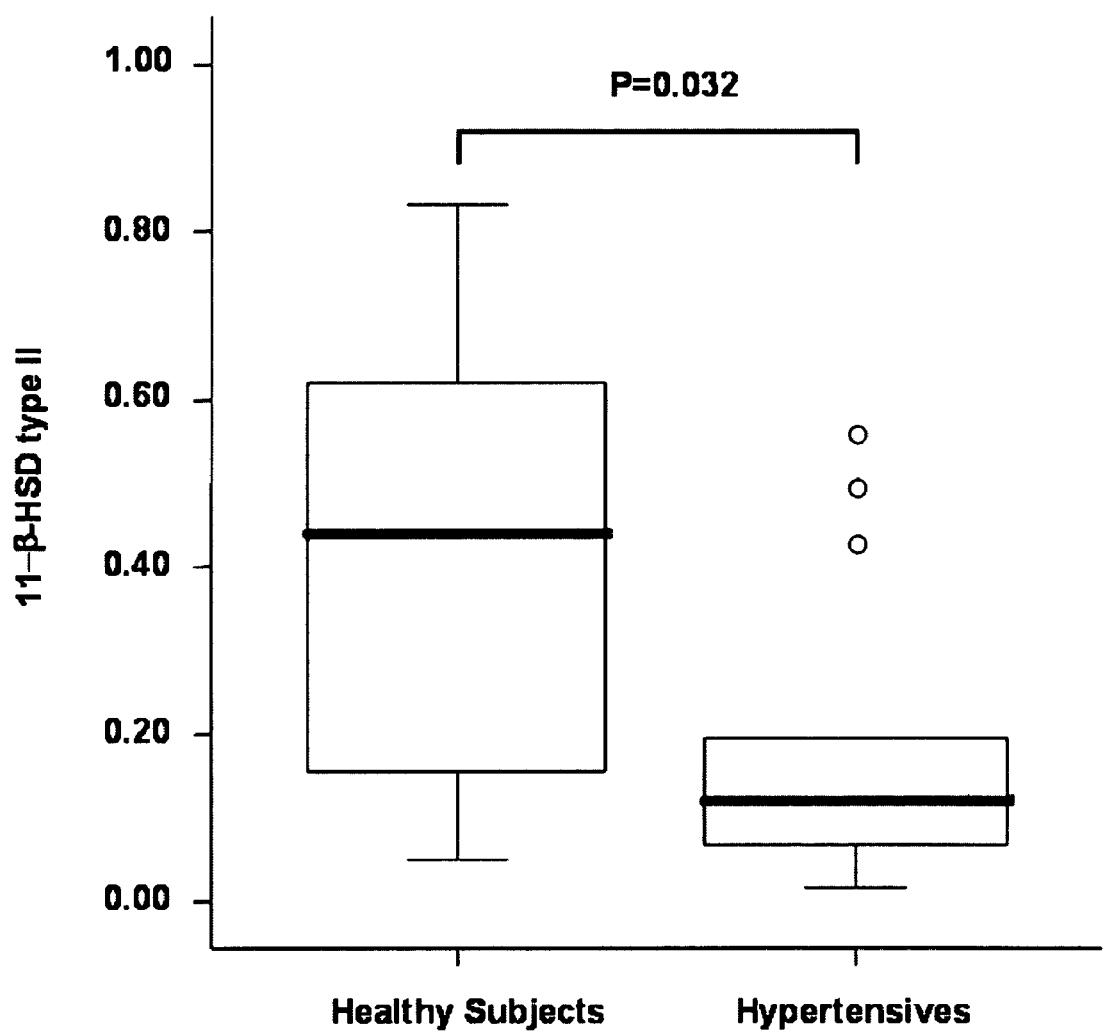
FIG. 12. Cell-free mRNA for 11β-HSD type II in healthy and in hypertensive subject, normalized against β-actin.

FIG. 11 shows the levels of whole blood mRNA for 11β-HSD type II in the two groups. The levels of mRNA in the hypertensive patients were higher than in controls, but the results did not reach significance. FIG. 12 shows the levels of mRNA for 11β-HSD type II in cell-free plasma. The levels of mRNA in the hypertensive patients (median: 0.18) were significantly (P=0.032) lower than in controls (median: 0.42).

Female patients had lower plasma β-globin (median: 561 genome equivalents/mL) compared to male patients (median: 736 genome equivalents/mL). On the other hand, healthy female subjects showed higher plasma β-globin (median: 1163 genome equivalents/mL) than did male subjects (median: 960 genome equivalents/mL). However, these differences were not statistically significant. Black patients showed a lower level of β-globin in cell-free plasma (median: 548 genome equivalents/mL) compared to caucasians (median: 653 genome equivalents/mL). On the other hand, black control subjects showed higher levels of β-globin (median: 1113 genome equivalents/mL) than caucasian (median: 959 genome equivalents/mL) subjects. However, none of these differences reached statistical significance.

Discussion

In the present study mRNA for 11β-HSD type 2 in whole blood and cell-free plasma and plasma DNA were measured in patients with hypertension.

Plasma DNA has been postulated to be a marker of cell death. Previous studies on DNA levels investigating various diverse diseases have reported higher DNA levels in patients compared to controls (9). Therefore, according to the stated hypothesis, increased cell death and, in turn, increased cell-free plasma DNA should be indicative of severity of disease or disorder. However, in contrast to previous studies comparing a pathologic group with healthy controls, a significant decrease was found in the DNA levels, as measured by β-globin levels (P=0.016) in the hypertensive group compared to healthy controls. To the best of our knowledge, this is the first documented use of real time RT-PCR for the detection and quantification of cell-free plasma nucleic acids in hypertensive patients in the absence of any other co-morbidity.

The lower levels of cell-free plasma DNA may be explained by the suggestion that the DNA is cleared faster from circulation in hypertensives compared to healthy controls. However, no evidence has been offered so far for the validation of this theory.

Another suggestion could be that DNase activity is increased in hypertensive patients. Thus, this may lead to a decrease in the levels of DNA in circulation as the nucleic acid would be degraded quicker in hypertensives. The same result could also be brought about by the incomplete or decreased formation of nucleosomes in hypertensives. The overall effect of this would result in increase of DNase and decreased DNA levels in the circulation for these patients. The opposite effect—a decrease in DNase, and thus an increase in DNA—has been noted in patients with malignant gastrointestinal disease (10).

A possible confounding factor in this study is the fact that all the patients recruited for this study were on drug therapy for hypertension. It is possible that hypertensive therapy decreases the apoptotic phenomena in the cell, thereby stabilizing the DNA levels and preventing release into the extracellular compartment.

The mRNA results showed that 11β-HSD type II was detected and quantified in the whole blood and in the cell-free plasma of all healthy individuals and hypertensive patients. There was a nonsignificant increase in the levels of whole blood 11β-HSD type II mRNA in hypertensive patients compared to healthy control subjects. It is known that the 11β-HSD type II is mostly found in kidney cells, but is also seen in smaller amounts in other tissues such as salivary glands, colon, and parotid glands. Since 11β-HSD type II mRNA was measured in whole blood, there was no way of excluding the presence of 11β-HSD type II mRNA derived from tissues other than kidney cells. This could explain the higher levels of whole blood 11β-HSD type II mRNA in hypertensives. However, given the lack of evidence to suggest that 11β-HSD type II mRNA expression from other tissues is modified in hypertension, in conjunction with the fact that the overwhelming majority of 11β-HSD type II mRNA is of renal origin, such an explanation is unlikely.

On the other hand mRNA levels of 11β-HSD type II in cell-free plasma were significantly lower in hypertensive patients. This is suggestive of a relationship between the mRNA for 11β-HSD type 2 and salt sensitivity. It is concluded that mRNA for 11β-HSD type 2 can be detected and that it is lower in hypertensive subjects.

REFERENCES

1. Poch, B. et al. 2001. Evaluation of renin-angintensin-aldotsterone system gene polymorphisms. *Hypertension* 38: 1204.
2. Lifton, R. P. 1996. Molecular genetics of blood pressure variation. *Science* 272: 676-680.
3. Lo, Y. M. & R. W. K. Chiu. 2004. The biology and diagnostic applications of plasma RNA. *Ann. N. Y. Acad. Sci.* 1022: 135-139.
4. Wijeratne, S. et al. Cell-free plasma DNA as a prognostic marker in intensive treatment unit patients. *Ann. N.Y. Acad. Sci.* 1022: 232-238.
5. Li, D. et al. 2004. Realtime quantitative PCR measurement of thyroglubulin mRNA in peripheral blood of thyroid cancer patients nd healthy subjects. *Ann. N. Y. Acad. Sci.* 1022: 147-151.
6. Hamaoui, K. et al. 2004. Real-time quantitative PCR measurement of circulatory rhodopsin mRNA in healthy subjects and patients with diabetic retinopathy. *Ann. N. Y. Acad. Sci.* 1022: 152-156.
7. The Sixth Report of the Joint National Committee on Prevention, Detection, Evaluation, and Treatment of High Blood Pressure (JNC VII). 1997. *Arch. Intern. Med.* 157: 2413-2446.
8. World Health Organisation, International Society of Hypertension Group. 2003. 2003 World Health Organisation (WHO)/International Society of Hypertension (ISH) Statement on Management on Hypertension. *J. Hypertens.* 21: 1983-1992.
9. Allen, K. C. et al. 2003. Cell-free nucleic acids in plasma, serum and urines a new tool in molecular diagnosis. *Ann. Clin. Biochem.* 40: 122-130.
10. Tamkovich, S. N. et al. 2005. Concentration of extracellular DNA and deoxyribonuclease activity in human blood. *Clin. Chem.* 51: 1317-1319.
11. Rainen, L. et al. 2002. Stabilisation of mRNA expression in whole blood samples. *Clin. Chem.* 48: 1883-1890.
12. Shalci, Z. 2004. Quantitative reverse transcription real-time PCR of circulating rhodopsin and RPE65 mRNA for the assessment of diabetic retinopathy. Department of Endocrinology, Diabetes and Metabolic Medicine, the Guy's, King's and St Thomas' School of Medicine University of London.
13. White, P. C., T. Mune & A. T. Agarwal. 1997. 11β-Hydroxysteroid dehydrogenase and the syndrome of apparent mineralocorticoid excess. *Endocrine Rev.* 18: 135-156.

Example 5

Circulating 11β-Hydroxysteroid Dehydrogenase Type I mRNA and Cardiovascular Risk Factors Summary 11β-hydroxysteroid dehydrogenase type I (11β-HSD1) has been implicated in the pathogenesis of central obesity and metabolic syndrome. It has been shown that tissue-specific mRNA is present in blood, raising the possibility that quantifiable levels of 11β-HSD1 mRNA may also be present in circulation. The aim of this study was to determine whether a relationship exists between circulating 11β-HSD1 mRNA levels and various cardiovascular risk factors. Whole blood was collected using PAXgene Blood RNA tubes from 73 subjects. Total RNA was extracted, reverse-transcribed to cDNA, and 11β-HSD1 mRNA was measured by quantitative real time PC. The median BMI was 24 (range=17-36) and the concentration of 11β-HSD1 mRNA tended to decrease with increasing BMI ($r=-0.206$; $P=0.08$). Multiple linear regression analysis identified BMI as an independent predictor of mRNA levels ($\beta=-0.412$, $P=0.002$). Other factors included in the analysis are age ($\beta=0.952$, $P<0.001$), smoking ($\beta=-0.228$, $P=0.027$), alcohol intake ($\beta=0.479$, $P<0.001$), and duration of menopause ($\beta=-1.602$, $P<0.001$). The results suggest a net decrease in systemic expression of 11β-HSD1 with increased smoking, BMI, and duration of menopause. Increased systemic expression is seen with increasing age and alcohol intake.

Introduction

The list of currently documented cardiovascular risk factors is wide and varied. It includes environmental factors—such as exercise, alcohol intake and smoking habits—and nonmodifiable factors such as age. In the past century, it has been noted that certain risk factors, namely obesity, dyslipidemia, and insulin resistance, tend to cluster together, forming a syndrome known as metabolic syndrome X (1).

It has been suggested that the enzyme, 11β-hydroxysteroid dehydrogenase type I (11β-HSD1) plays an important role in the pathogenesis of the metabolic syndrome, and that the enzyme's inhibition may be a plausible therapeutic target (2). This enzyme is responsible for converting glucocorticoids into their biologically active forms. The principle of hormone activation is not different from that seen with other steroid hormones; such as the conversion of testosterone to DHT, or estrogen to estradiol.

Cortisol is the main circulating glucocorticoid in humans. It has been demonstrated that the biological activity of any glucocorticoid relates to the presence of a hydroxyl group on carbon-11 of the steroid (3). Thus, cortisol, with a hydroxyl group on C-11, is the biologically active form of cortisone, where a C11 keto group is present. The enzymes responsible for the activation and deactivation of these steroids are the two isoforms of 11β-hydroxysteroid dehydrogenase: type 1 (11β-HSD1) and type 2 (11β-HSD2), respectively (4,5). Compromise in the activity of 11β-HSD2 results in the well characterized condition called "apparent mineralocorticoid excess."

Figure 13:
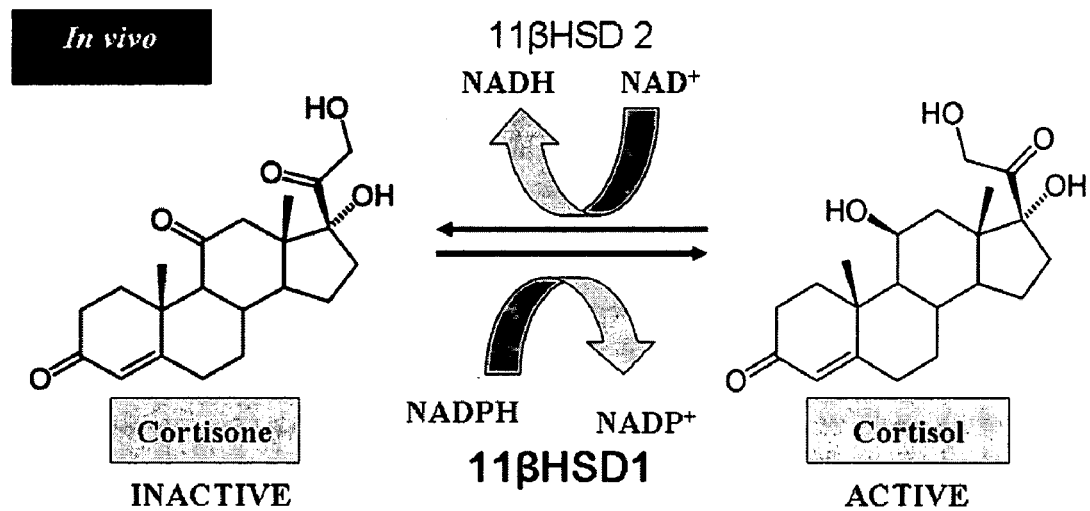
FIG. 13. The enzymatic actions of the two isoforms of 11β-hydroxysteroid dehydrogenase, 11βHSD1 and 11βHSD2. In vivo, 11βHSD1 catalyzes the conversion of inactive cortisone to active cortisol whereas 11β-HSD2 does the opposite. NADP+=oxidized nicotinamide adenine dinucleotide phosphate; NADPH=reduced nicotinamide adenine dinucleotide phosphate; NAD+=oxidized nicotinamide adenine dinucleotide; NADH=reduced nicotinamide adenine dinucleotide.

In vitro, 11β-HSD1 is a bidirectional enzyme, allowing both deactivation of cortisol and activation of cortisone. In vivo, however, it mainly acts as a reductase enzyme, converting cortisone to cortisol (FIG. 13) (6,7), It is thought that this is a consequence of its location—the lumen of the endoplasmic reticulum (8), where the required cofactor, reduced nicotinamide adenine dinucleotide phosphate (NADPH), is produced, tipping the redox scale towards the production of cortisol (6,7). 11β-HSD1 is expressed in virtually any tissue that responds to glucocorticoids; however, predominant expression appears to be in the liver, lungs, and adipose tissue (9).

Excess glucocorticoids are known to produce the features of Cushing's syndrome—such as central obesity, insulin resistance, hypertension, and dyslipidemia—many of which are similar to those seen in the metabolic syndrome. It follows that elevated expression of 11β-HSD1, resulting in increased bioavailability of active glucocorticoid at the tissue level, could play an important role in the pathogenesis of the metabolic syndrome and, hence, cardiovascular disease. The aim of this study was to detect and investigate the relationship between circulating 11β-HSD1 mRNA levels and various cardiovascular risk factors.

Materials and Methods

Subjects for the study were recruited from King's College London School of Medicine, and St. Thomas' Hospital. Ethical approval was obtained from the local Research Ethics Committee. Informed consent was obtained from all subjects. Subjects were excluded from the study if there was a history of systemic inflammatory conditions, such as systemic lupus erythematosus and rheumatoid arthritis, or if the drug history includes the use of systemic glucocorticoids. A total of 73 subjects were recruited.

Information on the subjects was collected in the form of a questionnaire filled out by the recruiter. This included age, BMI, duration of menopause, alcohol intake, and smoking habit.

Peripheral venous whole blood (5 mL) was collected directly into PAXgene™ Blood RNA tubes (Qiagen). These were stored at −80° C. until required for further processing. Whole blood RNA was extracted using the PAXgene Blood RNA Kit following the manufacturer's instructions. Extracted RNA was stored at −80° C. until required for reverse transcription of mRNA. cDNA synthesis was carried out using SuperScript II™ reverse transcriptase according to the manufacturer's instructions (Invitrogen). The generated cDNA was stored at −80° C. until further analysis.

Real-time quantitative PCR was used to detect and quantify the generated β-actin and 11β-HSD1 cDNA. β-actin was used to ensure that successful amplification has taken place and to normalize 11β-HSD1 mRNA levels. Amplification was undertaken in 96-well optical reaction plates using the ABI Prism_7000 Sequence Detection System (Applied Biosystems). This involved an initial phase of 2 min at 50° C. followed by 10 min at 95° C. and 40 cycles of 15 s at 95° C. and 1 mm at 60° C.

The assays for 11β-HSD-1 cDNA and β-actin cDNA for each sample were carried out on the same plate. Thus, on each plate, 16 samples were run, as well as two negative controls (NCs) of buffer BR5 (from the PAXgene Blood RNA Kit) to detect any cross-contamination. Furthermore, a 6-point standard curve for both assays using cDNA from healthy human liver. All samples, controls, and standard curve were assayed in duplicate.

For 11β-HSD1 mRNA, each well had either 10 μL of sample (or standard or negative control) and 40 μL and master mix solution. The master mix solution consists of 25 μl TaqMan® Universal Master Mix, forward and reverse primers at a concentration of 250 nM, and probe at 900 nM. For β-actin assay a Predeveloped TaqMan® Assay reagent that contained all the required primers and probes was used.

11β-HSD1 mRNA levels are expressed as the ratio to total whole blood β-actin levels. This is to ensure that procedural losses were accounted for. The inter- and intra-assay coefficients of variation (CV) for the real-time PCR technique were determined. For the calculation of the intra-assay CV, the values used were those of a sample that was analyzed 10 times in one plate for both assays. To determine inter-assay CV, the same sample was analyzed in duplicate over 10 different plates.

Statistical analysis was performed using SPSS version 14.0. Where appropriate, the tests used include the Mann-Whitney Utest, Kruskal-Wallis test, and standard multiple linear regression analysis. Significance was defined as P<0.05.

Results mRNAs for 11β-HSD1 and β-actin were detected in all the samples. The intra-assay coefficient of variation of the real-time PCR technique was 3.2% and 5.4% for 11β-HSD1 and β-actin, respectively. Inter-assay CVs were 6.5% and 8.5% for these markers, respectively.

Of the 73 recruited subjects, 58 were female. The median age of subjects was 58.5 years (range=20-86), and the median BMI was 23.9 (range=17-36) (Table 5).

TABLE 5

Characteristics of Subjects Studied

| Characteristics | Subjects (n = 73) |
|---|---|
| Median age (yr) (range) | 58.5 (20-86) |
| Sex (M:F) | 15:58 |
| Median BMI (kg/m2) (range) | 23.9 (17-36) |
| Median duration of menopause (range) | 22 (1-46) |

Figure 14:
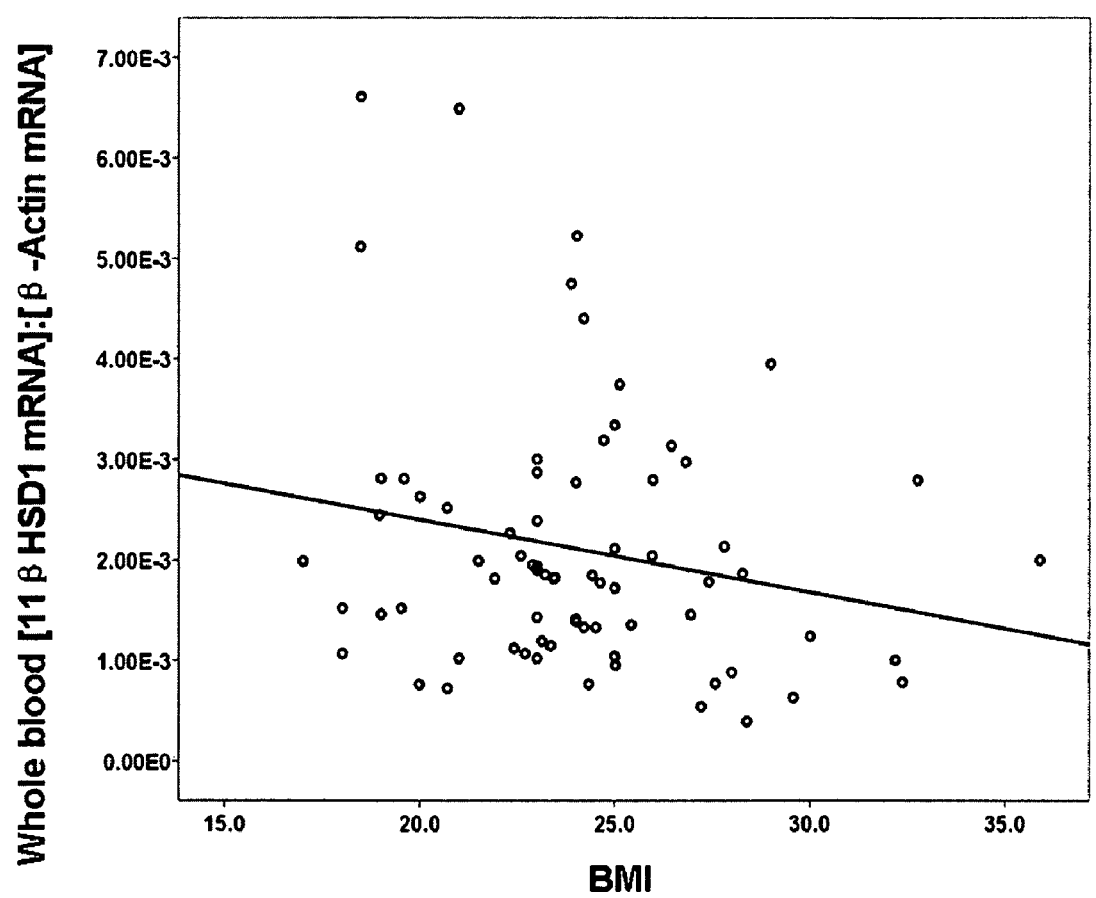
FIG. 14. Relationship between whole blood 11 β-HSD1 levels and BMI. Pearson correlation coefficient=−0.206; P=0.08; n=73.
Figure 15:
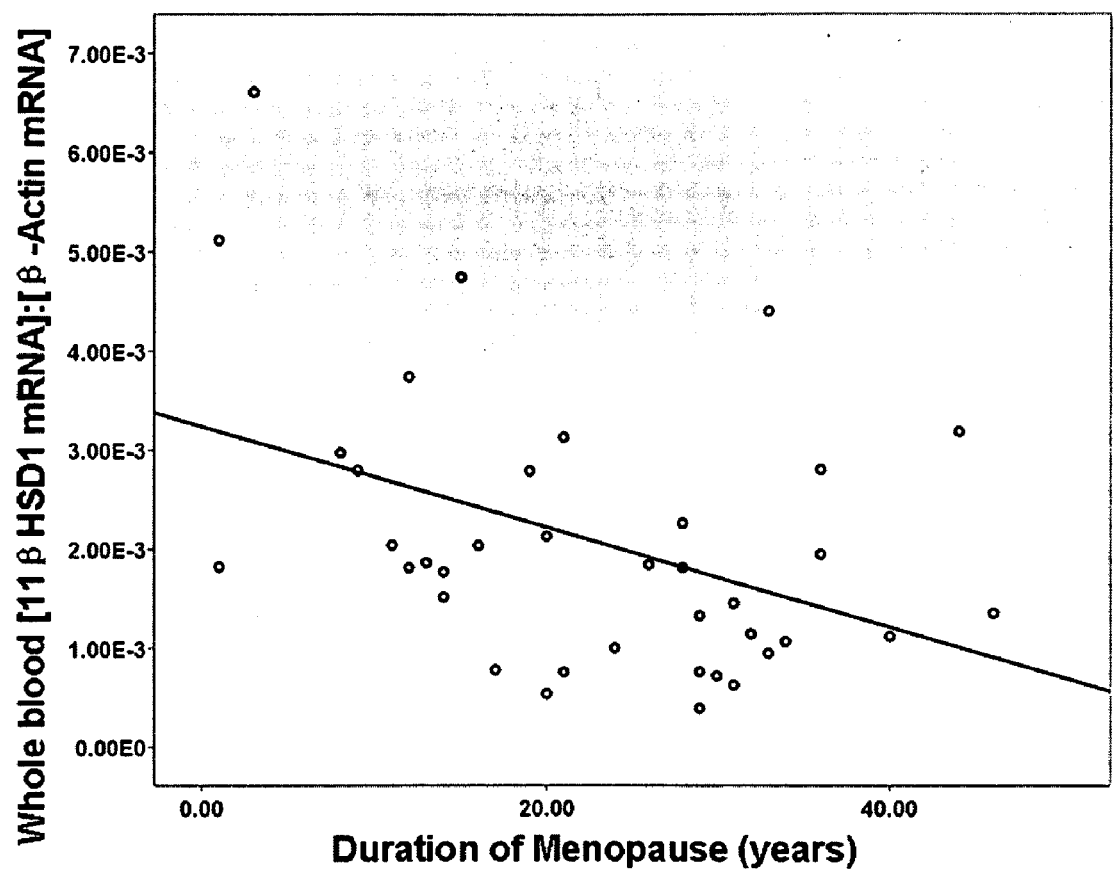
FIG. 15. The relationship between whole blood 11β-HSD1 mRNA levels and duration of menopause. Pearson correlation coefficient=−0.422; P=0.008; n=38.
Figure 16:
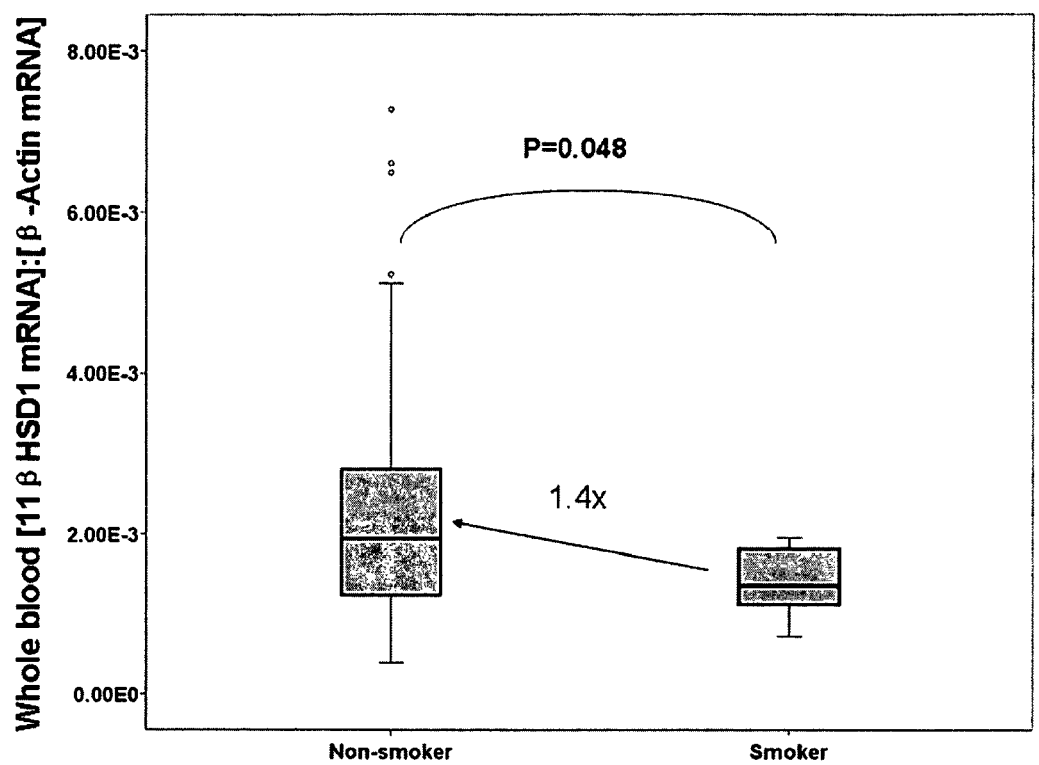
FIG. 16. Whole blood 11 β-HSD1 levels versus smoking habits. Levels are 1.4-fold lower in smokers; P=0.048.

Whole blood 11β-HSD1 mRNA levels showed an inverse relationship with BMI (r=−0.206) (FIG. 14). However, this did not reach statistical significance (P=0.08). FIG. 15 shows that an inverse relationship was also seen with duration of menopause (n=38, r=−0.422). This was highly significant (P=0.008). Blood 11β-HSD1 mRNA levels in smokers were 1.4-fold lower than in non-smokers (P=0.048) (FIG. 16).

Standard multiple linear regression analysis was undertaken to determine the factors that independently predict circulating 11β-HSD1 mRNA levels. The factors investigated were age, BMI, smoking habits, alcohol intake, and duration of menopause. The results summarized in Table 6 show that BMI is an independent predictor of mRNA levels (β=−0.412, P=0.002). Age (β=0.952, P<0.001), smoking status (β=−0.228, P=0.027), alcohol intake (β=0.479, P<0.001), and duration of menopause (β=−1.602, P<0.001) were also related to 11β-HSD1 mRNA levels.

TABLE 6

Multiple Linear Regression Analysis with 11β-HSD1 mRNA Levels as the Dependent Factor

| Characteristics value | β | P |
|---|---|---|
| Age | 0.952 | <0.001 |
| BMI | −0.412 | 0.002 |
| Smoking habits | −0.288 | 0.027 |
| Alcohol intake | 0.479 | <0.001 |
| Duration of menopause | −1.062 | <0.001 |

Discussion

The prevalence of the metabolic syndrome appears to increase with menopause, even when confounding factors such as BMI and age are taken into consideration (10). Thus, an increased expression of 11β-HSD1mRNA would be expected in women with a longer-duration menopause. However, our results do not show this (r=−0.422, P=0.008). This may be as a result of confounding factors, such as the use of hormone replacement therapy, or these results may genuinely reflect some association with estrogen deficiency. There have not been many studies that look at the effects of estrogens on 11β-HSD1 expression. Results from animal and human studies, and from various tissues demonstrate a variable impact of estrogens on expression. It has been shown in rats that estradiol decreases 11β-HSD1 activity in the liver (11) as well as decreasing 11β-HSD1 mRNA and protein expression in the kidney (12). Conversely, in baboon placental cells, estradiol appears to induce the reporter gene incorporating the 5'-flanking region of the 11β-HSD1 gene (13). More recently, it has been shown that estradiol strongly stimulates 11β-HSD1mRNA expression in the pre-adipocytes of women, but not men (14). The effect of estradiol on 11β-HSD1 expression in various tissues warrants more investigation.

There was a trend of decreasing 11β-HSD1 mRNA levels with increasing BMI (Pearson correlation coefficient=−0.206; P=0.08). This was also unexpected, considering the attention given to the enzyme's potential role in obesity and the metabolic syndrome. Activity and expression of this enzyme has been noted to be higher in the metabolically active omental fat than in subcutaneous adipose tissue (15). This, and the known effects of glucocorticoids on fat distribution (e.g., as seen in Cushing's syndrome), has prompted the suggestion that increased 11β-HSD1 expression is an important part of the pathogenesis of central obesity.

However, it seems that the effects of obesity on 11β-HSD1 expression are tissue-specific: it is generally seen to increase in adipose tissue, but decrease in the liver (16). It has been consistently shown that the liver's metabolism of cortisone to cortisol is impaired in obese individuals (17-19). However, activity of 11β-HSD1 in obesity appears to be tissue-specific. Rask et al. demonstrated that 11β-HSD1 activity is positively related to BMI in men and women (18,19). As for systemic activity of 11β-HSD1 the results of our study support the findings by Stewart et at al., who found a decrease in activity with obesity (17). This decrease in systemic activity, especially that resulting from liver, could serve as a protective mechanism against the harmful metabolic effects of obesity (6).

Studies on the effects of alcohol on 11⊖-HSD1 are limited. However, several papers report inhibition of the 11β-HSD2 isoenzyme (20-22). Our study demonstrates that increasing alcohol intake increases systemic expression of 11β-HSD1 (Table 6). The mechanism by which this happens is unclear. Nammi et al. found that in utero exposure of rats to alcohol resulted in increased activity of 11β-HSD1 (23). They postulate that the increased activity is linked to increased hexose-6-phosphate dehydrogenase (H6DP) expression. This enzyme increases the NADPH/NADP ratio in the ER luminal space where 11βHSD1 is found, thus tipping the redox scale and favoring increased activity of 11β-HSD1.

Whole blood 11β-HSD1 mRNA levels also appear to be decreased in smokers than in nonsmokers (P=0.046). The expression of this enzyme in the human lung has been demonstrated by RT-PCR, Northern blot, and immuno histochemical analyses (24). It has been implicated in the detoxification of the tobacco specific nitrosamine, 4-methylnitrosamino-1-(3-pyridyl)-1-butanone (NNK), the most potent carcinogen in cigarette smoke (24). It is possible that the chronic tissue damage caused by smoking reduces the ability of the ling to produce this enzyme, and hence reduces circulating levels of 11β-HSD1 mRNA. This could potentially form one of the mechanisms making smokers susceptible to lung cancer.

Finally, multiple linear regression analysis was undertaken to determine which factors independently predict whole blood 11β-HSD1 mRNA levels. Age, BMI, smoking habits, alcohol intake, and duration of menopause all did so. Increasing age and alcohol intake were associated with increased levels of circulating 11β-HSD1 mRNA, whereas increasing BMI, cigarette smoking, and duration of menopause are associated with decreased mRNA levels. The results showing a positive correlation with age may partly explain the increased metabolic effects seen in the elderly, such as insulin resistance.

REFERENCES

1. Peters, A. L. 2007. Identification of appropriate patients for cardiometabolic risk management. *Rev. Cardiovasc. Med.* 8(Suppl 4): S9-16.
2. Tomlinson, J. W. & P. M. Stewart. 2005. Mechanisms of disease: selective inhibition of 11β-hydroxysteroid dehydrogenase type 1 as a novel treatment for the metabolic syndrome. *Nat. Clin. Pract. Endocrinol. Metab.* 1: 92-99.
3. Cope, C. L. & E. Black. 1958. The production rate of cortisol in man. *Lancet* 14; 1020-1024.
4. Stewart, P. M. 1996. 11⊖-Hydroxysteroid dehydrogenase: implications for clinical medicine. *Clin. Endocrinol* 44: 493-499.
5. White, P. C. et al. 1997. 11⊖-Hydroxysteroid dehydrogenase and the syndrome of apparent mineralocorticoid excess. *Endocr. Rev.* 18: 355-361.
6. Tomlinson, J. W. et al. 2004. 11β Hydroxysteroid dehydrogenase type 1: a tissue-specific regulator of glucocorticoid response. *Endocr. Rev.* 25: 831-866.
7. Draper, N. & P. M. Stewart. 2005. 11β Hydroxysteroid dehydrogenase and pre-receptor regulation of corticosteroid hormone action. *J. Endocrinol.* 186: 251-271.
8. Odermett, A. et al. 2006. Why is 11β-hydroxysteroid dehydrogenase type 1 facing the endoplasmic reticulum lumen? Physiological relevance of the membrane topology of 11β-HSD1. *Mol. Cell. Endocrinol.* 248:15-23.
9. Bruley, C. et al. 2006. A novel promoter for the 11β-hydroxysteroid dehydrogenase type 1 gene is active in lung and is C/EBPα independent. *Endocrinology* 147: 2879-2885.
10. Carr, M. C. 2003. The emergence of metabolic syndrome with menopause. *J. Clin. Endocrinol. Metab.* 88: 2404-2411.
11. Low, S. C. et al. 1993. Regulation of 11β-hydroxysteroid dehydrogenase by sex steroids in vivo: further evidence for the existence of a second dehydrogenase in rat kidney. *J. Endocrinol.* 139: 27-35.
12. Gomez-Sanchez, E. P. et al. 2003. Regulation of 11β-hydroxysteroid dehydrogenase enzymes in the rat kidney by estradiol. *Am. J Physiol. Endocrinol. Metab.* 285: E272 E279.
13. Pepe, G. J. et al. 1999. Cloning of the 11betahydroxysteroid dehydrogenase (11beta-HSD)-2 gene in the baboon: effects of estradiol on promoter activity of 11beta-HSD-1 and -2 in placental JEG-3 cells. *Biochim. Biophys. Acta* 1444: 101-110.
14. Dieudonn'e, M. N. et al. 2006. Sex steroids and leptin regulate 11beta-hydroxysteroid dehydrogenase I and P450 aromatase expressions in human preadipocytes: sex specificities. *J. Steroid Biochem. Mol. Biol.* 99: 189-196.
15. Bujalska, I. J. et al. 1997. Does central obesity reflect "Cushing's disease of the omentum"? *Lancet* 349: 1210-1213.

16. Walker, B. R. & R. Andrew. 2006. Tissue production of cortisol by 11β-hydroxysteroid dehydrogenase type 1 and metabolic disease. *Ann. N.Y. Acad. Sci.* 1083: 165-184.
17. Stewart, P. M. et al. 1999. Cortisol metabolism in human obesity: impaired cortisone to cortisol conversion in subjects with central adiposity. *J. Clin. Endocrinol. Metab.* 84: 1022-1027.
18. Rask, E. et al. 2001. Tissue-specific dysregulation of cortisol metabolism in human obesity. *J. Endocrinol. Metab.* 86: 1418-1421.
19. Rask, E. et al. 2002. Tissue specific changes in peripheral cortisol metabolism in obese women: increased adipose 11β-hydroxysteroid dehydrogenase type 1 activity. *J. Cin. Endocrinol. Metab.* 87: 3330-3336.
20. Riddle, M. C. & P. A. McDaniel. 1993. Acute reduction of renal 11β-hydroxysteroid dehydrogenase activity by several anti-natriuretic stimuli. *Metabolism* 42: 1370-1374.
21. Valentino, R. et al. 1995. Alcohol inhibits 11β-hydroxysteroid dehydrogenase activity in rat kidney and liver. *Horm. Res.* 43: 176-180.
22. Zhang, Y et at. 2001. Effects of alcohol on blood pressure and production of vascular aldosterone and corticosterone. *Horm. Res.* 55: 245-248.
23. Nammi, S. et al. 2006. Increased 11β-hydroxysteroid dehydrogenase type-1 and hexose-6-phosphate dehydrogenase in liver and adipose tissue of rat offspring exposed to alcohol in utero. *Am. J. Physiol. Regul. Integr. Comp. Physiol.* 292: R1101-R1109.
24. Maser E. et al. 2006. 11β-Hydroxysteroid dehydrogenase type 1: purification from the liver and characterization as carbonyl reductase of xeniobiotics. *Mol. Cell. Endocrinol.* 24: 34-37.

Example 6

Circulating mRNA in the Assessment of Congestive Heart Failure

Introduction

Tissue-specific mRNA has recently been shown to be present in circulation and levels found to significantly higher in pathological states compared to healthy controls. In the present study we investigated circulating mRNAs in congestive heart failure (CHF). The aim of this study was to develop a novel molecular test for the assessment of congestive heart failure by measuring cardiac specific mRNA in peripheral blood.

Methods

Peripheral vein blood samples were collected from healthy controls (n=17) and confirmed congestive heart failure patients from the Heart Failure clinic in St Thomas' Hospital (n=41), into PAXgene Blood RNA tubes. Exclusion criteria were recent coronary intervention, myocardial ischemia, end-stage renal failure, and significant pulmonary diseases.

RNA was extracted following manufacturer's recommendation (Qiagen) and subsequently reverse transcribed to cDNA prior to analysis by real time quantitative PCR Serial dilution of human cardiac cDNA was used to develop a standard curve over the range: 0.00488-20.0 ng/ml. Standards and samples were measured in duplicate.

Results

Figure 17:
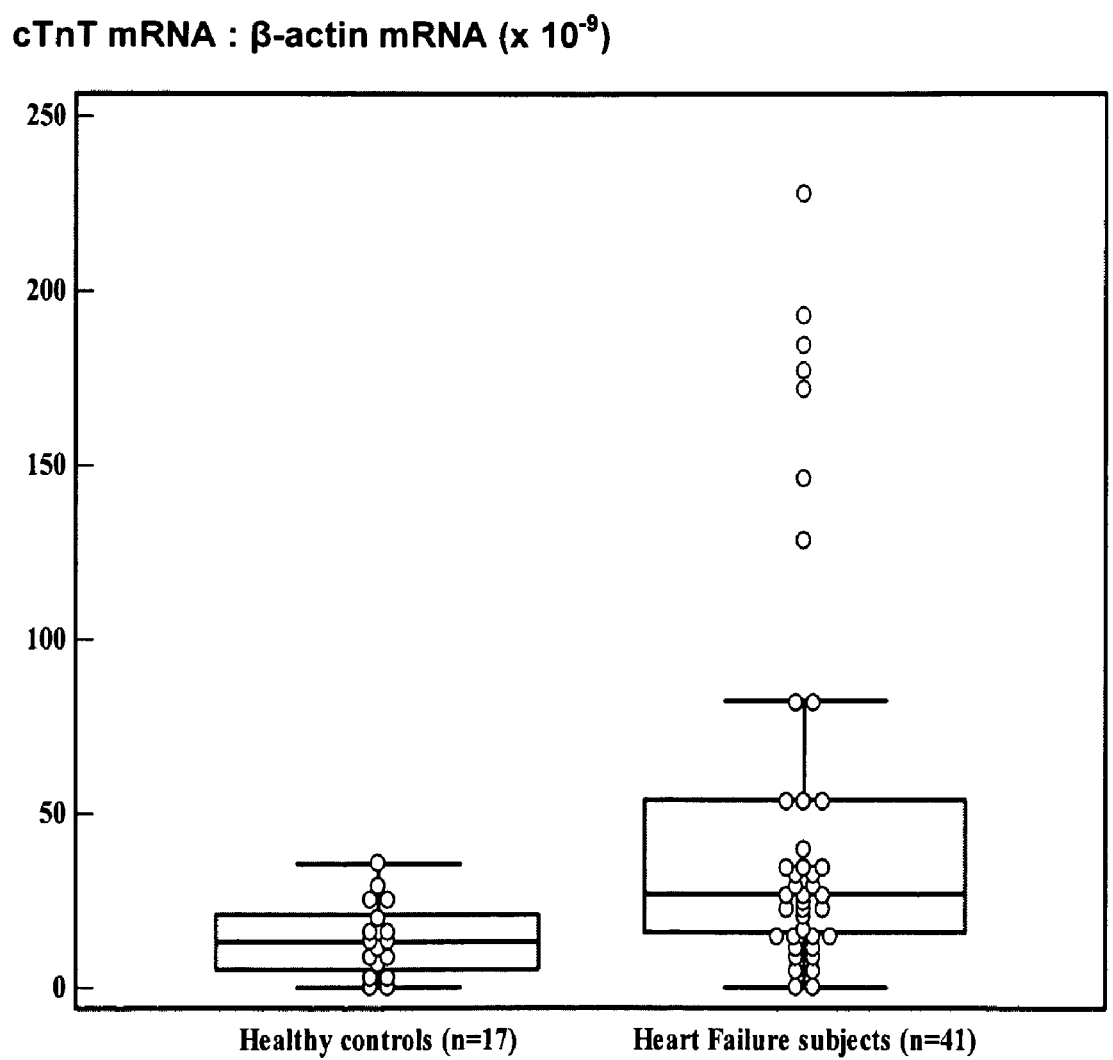
FIG. 17 Circulating cardiac troponin T (cTnT) mRNA in healthy controls and heart failure patients.
Figure 18:
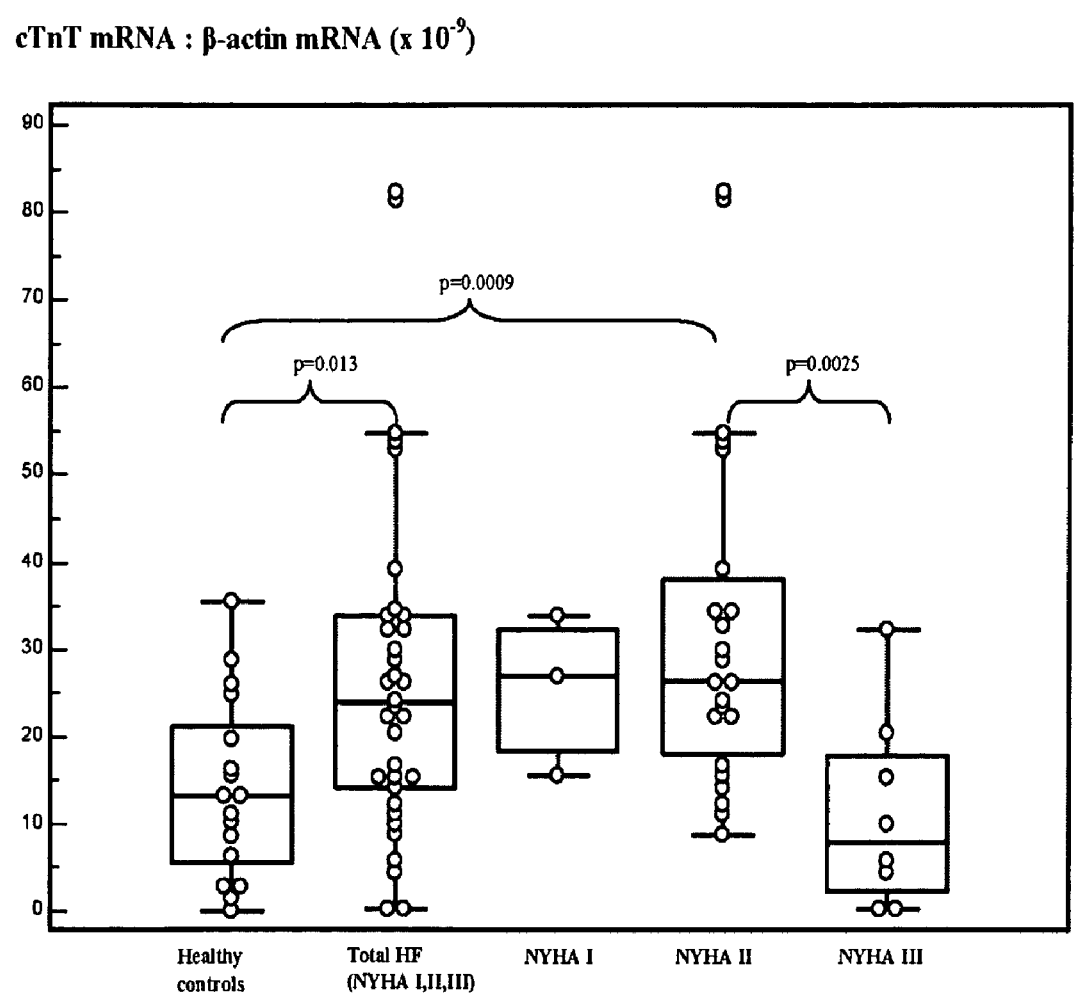
FIG. 18 Circulating cardiac troponin T (cTnT) mRNA in healthy controls and heart failure patients in individual NYHA class.

As shown in FIG. 17 and Table 7, the mean cardiac troponin T (cTnT) mRNA marker level in the heart failure group (mean concentration 1.66 pg/ml, range 1.04-2.28 pg/ml, 95% C.I.) was found to be significantly higher p<0.01) than the level in healthy controls (mean concentration 0.50 pg/ml, range 0.19-0.82 pg/ml, 95% CI).

Circulating cardiac troponin T (cTnT) mRNA is three times higher in HF patients compared to control. A higher cTnT mRNA levels suggests poorly controlled heart failure (from clinical data). cTnT mRNA levels are significantly lower in NYHA class III compared to NYHA I-II patients. A possible explanation may be intensification of treatment in this group and/or reduction of functional myocytes in this group of patient.

Conclusions

Circulating cTnT mRNA can be detected and quantified in healthy and heart failure subjects. cTnT mRNA levels is significantly higher in heart failure subjects compared to healthy controls. This marker has prognostic and diagnostic uses and may be used for assessing severity of heart failure and the level of control achieved.

TABLE 7

Characteristics of heart failure subjects and healthy controls

| | Healthy controls | Heart failure subjects |
|---|---|---|
| Number | 17 | 41 |
| Male/Female, n | 7/10 | 32/9 |
| Age, median (range) | 41 (26-60) | 70 (24-86) |
| Diabetes Mellitus, n (%) | 0 | 10 (24.4) |
| Hypertension, n (%) | 0 | 19 (46.3) |
| Ischaemic CMP | 0 | 23 (56.1) |
| Idiopathic dilated CMP | 0 | 3 (7.3) |
| NYHA Functional Class | | |
| NYHA I, n(%) | — | 3 (7.3) |
| NYHA II, n(%) | — | 30 (73.2) |
| NYHA III, n(%) | — | 8 (19.5) |
| Plasma NT-proBNP, pmol/l (median ± 2S.E.). Sensitivity 6 pmol/l | <6 | 326 ± 102 |
| Number of detectable serum cTnT, ng/ml. Sensitivity 0.01 ng/ml | 0 (0.0%) | 8 (23.5%) |
| 2-D Echocardiographic Ejection Fraction (%) | — | 31 ± 18 |

Biomarker Gene and Primer Sequences

Table 8 below shows database accession numbers of the biomarkers of the present invention. The sequences of PCR primers suitable for their amplification are also given, e.g. as used in the above examples. The invention may be performed using the primers disclosed below or a skilled person may design and use alternative primers, for instance based on the sequences of the biomarker genes listed in the database.

TABLE 8

Database accession numbers of biomarkers and PCR primers

| Accession No | Gene | Oligonucleotide | Oligo Sequence |
|---|---|---|---|
| NM_000539 | Rhodopsin | RH613-F | CCG GCT GGT CCA GGT ACA T |
| | | RH694-R | TTG TTG ACC TCC GGC TTG AG |
| | | RH642-T | CTG CAG TGC TCG TGT GGA ATC GAC TAC C |
| NM_000329 | RPE65 | R282-F | TGT CAC ATA CCA CAG AAG GTT CAT C |
| | | R366-R | GCC AAA TTC TGT TAT GAC GAT CCT |
| | | R311-T | CTG ATG CTT ACG TAC GGG CAA TGA CTG AG |
| NM_000330 | Retinoschisin | Ret159-F | TGC CAC CTC CTT GGA CTG TAT |
| | | Ret230-R | GTG ACC TCC CCT GAC TCG AA |
| | | Ret183-T | AGA ATG CCC ATA TCA CAA GCC TCT GGG |
| NM_001975 | Neurone Specific Enolase | ENO-365F | AGCTGAGGGATGGAGACAAACA |
| | | ENO-443R | GCGATGGTGGAGTTGATGTG |
| | | ENO-388T | CGTTACTTAGGCAAAGGTGTCCTGAAGGCA |
| NM_000364 | Troponin T | TNN-F | GGTCGTTCATGCCCAACTTG |
| | | TNN-R | CCGGTGGATGTCATCAAAGTC |
| | | TNN-T | TGCCTCCCAAGATCCCCGATGG |
| NM_000196 | 11-β-Hydroxysteroid dehydrogenase Type 2 | HSD2-F | CCGTATTGGAGTTGAACAGCC |
| | | HSD2-R | CAACTACTTCATTGTGGCCTGC |
| | | HSD2-T | CTAGAGTTCACCAAGGCCCACACCACC |
| NM_005525 | 11-β-Hydroxysteroid dehydrogenase Type 1 | HSD1-257F | GGC TTA TCA TCT GGC GAA GAT G |
| | | HSD1-336R | GGG ATA CCA CCT TCT GTA GAG TTT CT |
| | | HSD1-281T | AGC CCA TGT GGT GGT GAC AGC G |
| *From Lo et al, 2000 | β-Globin | BG354-F | GTG CAC CTG ACT CCT GAG GAG A |
| | | GB455-R | CCT TGA TAC CAA CCT GCC CAG |
| | | BG402-T | AAG GTG AAC GTG GAT GAA GTT GGT GG |

*Plasma DNA as a Prognostic Marker in Trauma Patients. (2000). Y. M. Dennis Lo, Timothy H. Rainer, Lisa Y. S. Chan, N. Magnus Hjelm and Robert A. Cocks ClinicalChemistry. 46: 319-323

Each of the applications and patents mentioned in this document, and each document cited or referenced in each of the above applications and patents, and any manufacturer's instructions or catalogues for any products cited or mentioned in each of the applications and patents and in any of the application cited documents, are hereby incorporated herein by reference Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments and that many modifications and additions thereto may be made within the scope of the invention. Indeed, various modifications of the described modes for carrying out the invention which are obvious to those skilled in molecular biology or related fields are intended to be within the scope of the claims. Furthermore, various combinations of the features of the following dependent claims can be made with the features of the independent claims without departing from the scope of the present invention.

What is claimed is:

1. A method for assessing susceptibility to a condition associated with metabolic syndrome in a subject, comprising determining a level of at least one mRNA in the subject's blood, wherein the at least one mRNA encodes RPE65 protein and the condition is at least one of diabetes mellitus, diabetic retinopathy, and diabetic mellitus without retinopathy, and determining the subject's susceptibility to said condition based on the level of said at least one mRNA.

2. The method of claim 1, wherein an increase in the level of RPE65 mRNA relative to a control level is indicative of diabetic retinopathy.

3. The method of claim 1, wherein an increase in the level of RPE65 relative to a control level is indicative of proliferative retinopathy.

4. The method of claim 1, wherein the at least one mRNA further comprises an mRNA that encodes retinoschisin protein.

5. The method of claim 4, wherein an increase in the level of retinoschisin mRNA relative to a control level is indicative of diabetes mellitus without retinopathy.

6. The method of claim 4, wherein a decrease in retinoschisin mRNA relative to a control level is indicative of diabetes mellitus with retinopathy.

7. The method of claim 1, wherein the level of mRNA is determined by reverse transcription polymerase chain reaction.

8. The method of claim 1, wherein the level of mRNA is determined in whole blood or in plasma.

* * * * *

SEQUENCE LISTING

<160> NUMBER OF SEQ ID NOS: 24

<210> SEQ ID NO 1
<211> LENGTH: 19
<212> TYPE: DNA
<213> ORGANISM: Artificial

```
<220> FEATURE:
<223> OTHER INFORMATION: Synthetic sequence

<400> SEQUENCE: 1
ccggctggtc caggtacat                                                    19

<210> SEQ ID NO 2
<211> LENGTH: 20
<212> TYPE: DNA
<213> ORGANISM: Artificial
<220> FEATURE:
<223> OTHER INFORMATION: Synthetic sequence

<400> SEQUENCE: 2
ttgttgacct ccggcttgag                                                   20

<210> SEQ ID NO 3
<211> LENGTH: 28
<212> TYPE: DNA
<213> ORGANISM: Artificial
<220> FEATURE:
<223> OTHER INFORMATION: Synthetic sequence

<400> SEQUENCE: 3
ctgcagtgct cgtgtggaat cgactact                                          28

<210> SEQ ID NO 4
<211> LENGTH: 25
<212> TYPE: DNA
<213> ORGANISM: Artificial
<220> FEATURE:
<223> OTHER INFORMATION: Synthetic sequence

<400> SEQUENCE: 4
tgtcacatac cacagaaggt tcatc                                             25

<210> SEQ ID NO 5
<211> LENGTH: 24
<212> TYPE: DNA
<213> ORGANISM: Artificial
<220> FEATURE:
<223> OTHER INFORMATION: Synthetic sequence

<400> SEQUENCE: 5
gccaaattct gttatgacga tcct                                              24

<210> SEQ ID NO 6
<211> LENGTH: 29
<212> TYPE: DNA
<213> ORGANISM: Artificial
<220> FEATURE:
<223> OTHER INFORMATION: Synthetic sequence

<400> SEQUENCE: 6
ctgatgctta cgtacgggca atgactgag                                         29

<210> SEQ ID NO 7
<211> LENGTH: 21
<212> TYPE: DNA
<213> ORGANISM: Artificial
<220> FEATURE:
<223> OTHER INFORMATION: Synthetic sequence

<400> SEQUENCE: 7
tgccacctcc ttggactgta t                                                 21
```

<210> SEQ ID NO 8
<211> LENGTH: 20
<212> TYPE: DNA
<213> ORGANISM: Artificial
<220> FEATURE:
<223> OTHER INFORMATION: Synthetic sequence

<400> SEQUENCE: 8
gtgacctccc ctgactcgaa                                              20

<210> SEQ ID NO 9
<211> LENGTH: 27
<212> TYPE: DNA
<213> ORGANISM: Artificial
<220> FEATURE:
<223> OTHER INFORMATION: Synthetic sequence

<400> SEQUENCE: 9
agaatgccca tatcacaagc ctctggg                                      27

<210> SEQ ID NO 10
<211> LENGTH: 22
<212> TYPE: DNA
<213> ORGANISM: Artificial
<220> FEATURE:
<223> OTHER INFORMATION: Synthetic sequence

<400> SEQUENCE: 10
agctgaggga tggagacaaa ca                                           22

<210> SEQ ID NO 11
<211> LENGTH: 20
<212> TYPE: DNA
<213> ORGANISM: Artificial
<220> FEATURE:
<223> OTHER INFORMATION: Synthetic sequence

<400> SEQUENCE: 11
gcgatggtgg agttgatgtg                                              20

<210> SEQ ID NO 12
<211> LENGTH: 30
<212> TYPE: DNA
<213> ORGANISM: Artificial
<220> FEATURE:
<223> OTHER INFORMATION: Synthetic sequence

<400> SEQUENCE: 12
cgttacttag gcaaaggtgt cctgaaggca                                   30

<210> SEQ ID NO 13
<211> LENGTH: 20
<212> TYPE: DNA
<213> ORGANISM: Artificial
<220> FEATURE:
<223> OTHER INFORMATION: Synthetic sequence

<400> SEQUENCE: 13
ggtcgttcat gcccaacttg                                              20

<210> SEQ ID NO 14
<211> LENGTH: 21
<212> TYPE: DNA
<213> ORGANISM: Artificial
<220> FEATURE:
<223> OTHER INFORMATION: Synthetic sequence

```
<400> SEQUENCE: 14
ccggtggatg tcatcaaagt c                                              21

<210> SEQ ID NO 15
<211> LENGTH: 22
<212> TYPE: DNA
<213> ORGANISM: Artificial
<220> FEATURE:
<223> OTHER INFORMATION: Synthetic sequence

<400> SEQUENCE: 15
tgcctcccaa gatccccgat gg                                             22

<210> SEQ ID NO 16
<211> LENGTH: 21
<212> TYPE: DNA
<213> ORGANISM: Artificial
<220> FEATURE:
<223> OTHER INFORMATION: Synthetic sequence

<400> SEQUENCE: 16
ccgtattgga gttgaacagc c                                              21

<210> SEQ ID NO 17
<211> LENGTH: 22
<212> TYPE: DNA
<213> ORGANISM: Artificial
<220> FEATURE:
<223> OTHER INFORMATION: Synthetic sequence

<400> SEQUENCE: 17
caactacttc attgtggcct gc                                             22

<210> SEQ ID NO 18
<211> LENGTH: 27
<212> TYPE: DNA
<213> ORGANISM: Artificial
<220> FEATURE:
<223> OTHER INFORMATION: Synthetic sequence

<400> SEQUENCE: 18
ctagagttca ccaaggccca caccacc                                        27

<210> SEQ ID NO 19
<211> LENGTH: 22
<212> TYPE: DNA
<213> ORGANISM: Artificial
<220> FEATURE:
<223> OTHER INFORMATION: Synthetic sequence

<400> SEQUENCE: 19
ggcttatcat ctggcgaaga tg                                             22

<210> SEQ ID NO 20
<211> LENGTH: 26
<212> TYPE: DNA
<213> ORGANISM: Artificial
<220> FEATURE:
<223> OTHER INFORMATION: Synthetic sequence

<400> SEQUENCE: 20
gggataccac cttctgtaga gtttct                                         26

<210> SEQ ID NO 21
```

-continued

```
<211> LENGTH: 22
<212> TYPE: DNA
<213> ORGANISM: Artificial
<220> FEATURE:
<223> OTHER INFORMATION: Synthetic sequence

<400> SEQUENCE: 21
agcccatgtg gtggtgacag cg                                                22

<210> SEQ ID NO 22
<211> LENGTH: 22
<212> TYPE: DNA
<213> ORGANISM: Artificial
<220> FEATURE:
<223> OTHER INFORMATION: Synthetic sequence

<400> SEQUENCE: 22
gtgcacctga ctcctgagga ga                                                22

<210> SEQ ID NO 23
<211> LENGTH: 21
<212> TYPE: DNA
<213> ORGANISM: Artificial
<220> FEATURE:
<223> OTHER INFORMATION: Synthetic sequence

<400> SEQUENCE: 23
ccttgatacc aacctgccca g                                                 21

<210> SEQ ID NO 24
<211> LENGTH: 26
<212> TYPE: DNA
<213> ORGANISM: Artificial
<220> FEATURE:
<223> OTHER INFORMATION: Synthetic sequence

<400> SEQUENCE: 24
aaggtgaacg tggatgaagt tggtgg                                            26
```